(12) United States Patent
Zarrine-Afsar et al.

(10) Patent No.: US 10,441,668 B2
(45) Date of Patent: Oct. 15, 2019

(54) SYSTEM AND METHOD FOR ENHANCED MASS SPECTROMETRY IMAGING

(71) Applicant: University Health Network, Toronto (CA)

(72) Inventors: Arash Zarrine-Afsar, Toronto (CA); David Anthony Jaffray, Etobicoke (CA)

(73) Assignee: University Health Network, Toronto, Ontario (CA)

( * ) Notice: Subject to any disclaimer, the term of this patent is extended or adjusted under 35 U.S.C. 154(b) by 104 days.

(21) Appl. No.: 15/533,799

(22) PCT Filed: Dec. 8, 2015

(86) PCT No.: PCT/CA2015/051282
§ 371 (c)(1),
(2) Date: Jun. 7, 2017

(87) PCT Pub. No.: WO2016/090471
PCT Pub. Date: Jun. 16, 2016

(65) Prior Publication Data
US 2017/0368205 A1 Dec. 28, 2017

Related U.S. Application Data

(60) Provisional application No. 62/088,964, filed on Dec. 8, 2014.

(51) Int. Cl.
*A61K 49/10* (2006.01)
*A61K 49/00* (2006.01)
(Continued)

(52) U.S. Cl.
CPC .......... *A61K 49/106* (2013.01); *A61K 49/00* (2013.01); *A61K 49/0438* (2013.01);
(Continued)

(58) Field of Classification Search
USPC ................................. 250/281, 282
See application file for complete search history.

(56) References Cited

U.S. PATENT DOCUMENTS

| | | | |
|---|---|---|---|
| 2003/0153007 A1* | 8/2003 | Chen | C12Q 1/485 506/6 |
| 2003/0186326 A1* | 10/2003 | Regnier | C07K 1/13 435/7.1 |

(Continued)

FOREIGN PATENT DOCUMENTS

| | | |
|---|---|---|
| CA | 2900686 A1 | 8/2014 |
| CA | 2969251 A1 | 6/2016 |

(Continued)

OTHER PUBLICATIONS

Cooks et al., "Perspectives and retrospectives in mass spectrometry: one view", Eur J Mass Spectrom (Chichester, Eng), 2010, 16(3): 283-300.

(Continued)

*Primary Examiner* — Kiet T Nguyen
(74) *Attorney, Agent, or Firm* — Bereskin & Parr LLP/S.E.N.C.R.L., s.r.l.; Tony Orsi

(57) ABSTRACT

Various embodiments are described herein for a system and a method for identifying a region of interest in tissue using mass spectrometry. An agent administration component can be provided to administer an exogenous agent to the tissue. A sampling unit can also be provided to acquire a sample from the tissue. The sample can then be provided to a high sensitivity analysis platform, such as a mass analyzer, to analyze the sample and determine a distribution of the exogenous agent or a by-product of the exogenous agent within the tissue based on the analysis. The analysis platform can then identify the region of interest based on the distribution of the exogenous agent or the distribution of the by-product.

21 Claims, 19 Drawing Sheets

(51) Int. Cl.

| | | |
|---|---|---|
| *A61K 49/04* | (2006.01) | |
| *G01N 27/00* | (2006.01) | |
| *G01N 33/483* | (2006.01) | |
| *G01N 33/58* | (2006.01) | |
| *H01J 49/00* | (2006.01) | |
| *H01J 49/10* | (2006.01) | |

(52) U.S. Cl.
CPC ......... *G01N 27/00* (2013.01); *G01N 33/4833* (2013.01); *G01N 33/58* (2013.01); *H01J 49/0004* (2013.01); *H01J 49/105* (2013.01); *G01N 2458/15* (2013.01); *G01N 2560/00* (2013.01)

(56) References Cited

U.S. PATENT DOCUMENTS

| | | |
|---|---|---|
| 2005/0002859 A1 | 1/2005 | Marnett et al. |
| 2007/0141719 A1 | 6/2007 | Bui |
| 2008/0206131 A1 | 8/2008 | Jaffray et al. |
| 2010/0284934 A1 | 11/2010 | El-Agnaf |
| 2011/0064658 A1 | 3/2011 | Scherz et al. |
| 2011/0190145 A1 | 8/2011 | Caprioli |
| 2012/0020876 A1 | 1/2012 | Olive et al. |
| 2012/0156712 A1 | 6/2012 | Takats |
| 2012/0258485 A1 | 10/2012 | Stauber et al. |
| 2012/0326019 A1 | 12/2012 | Claude et al. |
| 2013/0224785 A1 | 8/2013 | Takats |
| 2013/0280820 A1* | 10/2013 | Beaumont .......... G01N 33/6881 436/501 |
| 2014/0363833 A1 | 12/2014 | Bhatia et al. |
| 2015/0287578 A1 | 10/2015 | Bendall et al. |
| 2017/0368205 A1 | 12/2017 | Zarrine-Afsar et al. |

FOREIGN PATENT DOCUMENTS

| | | |
|---|---|---|
| WO | 2010136887 A1 | 12/2010 |
| WO | 2013177385 A1 | 11/2013 |
| WO | 2014/175211 A1 | 10/2014 |
| WO | 2016/090471 A1 | 6/2016 |
| WO | 2017/049403 A1 | 3/2017 |

OTHER PUBLICATIONS

Eberlin et al., "Classifying human brain tumors by lipid imaging with mass spectrometry", Cancer Res, 2012, 72(3): 645-654.

Eberlin et al., "Ambient mass spectrometry for the intraoperative molecular diagnosis of human brain tumors", Proc Nati Acad Sci U S A, 2013, 110(5): 1611-1616.

Caravan et al., "Gadolinium (III) Chelates as MRI Contrast Agents: Structure, Dynamics and Applications", Chemical Reviews, 1999, 99(9): 2293-2352.

Cheng et al., "Magnetic Resonance Imaging (MRI) Contrast Agents for Tumor Diagnosis", J Healthc Eng, 2013, 4(1): 23-46.

Zheng et al., "PEGylated liposome co-encapsulating iohexol and gadoteridol for multimodal CT and MR imaging", Jul. 29, 2011 [Updated Sep. 2011]. In: Molecular Imaging and Contrast Agent Database (MICAD) [Internet]. Bethesda (MD): National Center for Biotechnology Information (US), pp. 2004-2013.

Zheng et al., "Liposome contrast agent for CT-based detection and localization of neoplastic and inflammatory lesions in rabbits: validation with FDG-PET and histology", Contrast Media Mol Imaging, 2010, 5(3): 147-154.

Zheng et al., "In Vivo Performance of a Liposomal Vascular Contrast Agent for CT and MR-Based Image Guidance Applications", Pharm Res, 2007, 24: 1193-1201.

Amini-Nik et al., "Ultrafast Mid-IR Laser Scalpel: Protein Signals of the Fundamental Limits to Minimally Invasive Surgery", PLoS One, 2010, 5(9): e13053, pp. 1-6.

Balog et al., "Intraoperative tissue identification using rapid evaporative ionization mass spectrometry", Sci Transl Med, 2013, 5(194): 194ra193. pp. 1-11.

Wong, "'Intelligent knife' tells surgeon if tissue is cancerous", Press Release, Imperial College London, UK, 2013 <http://www3.imperial.ac.uk/newsandeventspggrp/imperialcollege/newssummary/news_17-7- 2013-17-17-32>.

Xu et al., "Comparison of FDG whole-body PET/CT and gadolinium-enhanced whole-body MRI for distant malignancies in patients with malignant tumors: a meta-analysis", Ann Oncol., 2013, 24(1): 96-101.

International Search Report and Written Opinion dated Feb. 15, 2016 in related International Patent Application No. PCT/CA2015/051282.

Milne et al., "Lipidomics: an analysis of cellular lipids by ESI-MS", Methods, 2006, 39(2): 92-103.

Janfelt et al., "Displaced dual-mode imaging with desorption electrospray ionization for simultaneous mass spectrometry imaging in both polarities and with several scan modes", Journal of Mass Spectrometry, 2013, 48(3): 361-366.

Wiseman et al., "Tissue imaging at atmospheric pressure using desorption electrospray ionization (DESI) mass spectrometry", Angew Chem Int Ed Engl, 2006, 45(43): 7188-7192.

Forsythe et al., "Semitransparent Nanostructured Films for Imaging Mass Spectrometry and Optical Microscopy", Anal Chem., 2012, 84(24): 10665-10670.

LCGC Editors, "IC-ICP-MS Analysis of Gadolinium Based MRI Contrast Agents", 2011 <http://www.chromatographyonline.com/lc-Icp-ms-analysis-gadolinium-based-mri-contrast-agents-0>.

International Search Report and Written Opinion dated Nov. 30, 2016 in corresponding International Patent Application No. PCT/CA2016/051112.

Mclaughlin et al., "Influence of frozen-section analysis of sentinel lymph node and lumpectomy margin status on reoperation rates in patients undergoing breast-conservation therapy", J Am Coll Surg, 2008, 206(1): 76-82.

Abbas et al., "The incidence of carcinoma in cytologically benign thyroid cysts", Surgery, 2001, 130(6): 1035-1038.

Erguvan-Dogan et al., "Specimen radiography in confirmation of MRI-guided needle localization and surgical excision of breast lesions", AJR Am J Roentgenol, 2006, 187(2): 339-344.

Jolesz, "Intraoperative imaging in neurosurgery: where will the future take us?", Acta Neurochir Suppl , 2011, 109: 21-25.

Haka et al., "In vivo margin assessment during partial mastectomy breast surgery using raman spectroscopy", Cancer Res, 2006, 66(6): 3317-3322.

Van De Plas et al., "Image fusion of mass spectrometry and microscopy: a multimodality paradigm for molecular issue mapping", Nature Methods, 12(4): 366-372 (Mar. 5, 2014; published Feb./Apr. 2015).

Thomusch et al., "Intraoperative neuromonitoring of surgery for benign goiter", Am J Surg, 2002, 183(6): 673-678.

Curatolo et al., "Ultrasound-guided optical coherence tomography needle probe for the assessment of breast cancer tumor margins", AJR Am J Roentgenol, 2012, 199(4): W520-522.

Kennedy et al., "Needle optical coherence elastography for the measurement of microscale mechanical contrast deep within human breast tissues", J Biomed Opt, 2013, 18(12): 121510-1 to 121510-8.

Veselkov et al., "Chemo-informatic strategy for imaging mass spectrometry-based hyperspectral profiling of lipid signatures in colorectal cancer", Proc. Natl. Acad. Sci. U S A, 111(3): 1216-1221 (Jan. 21, 2014).

Mclaughlin et al., "Imaging of human lymph nodes using optical coherence tomography: potential for staging cancer", Cancer Res, 2010, 70(7): 2579-2584.

Mclaughlin et al., "Parametric imaging of cancer with optical coherence tomography", J Biomed Opt, 2010, 15(4): 046029-1 to 046029-4.

Gianfelice et al., "MR imaging-guided focused ultrasound surgery of breast cancer: correlation of dynamic contrast-enhanced MRI with histopathologic findings", Breast Cancer Res Treat, 2003, 82(2): 93-101.

Eberlin et al., "Molecular assessment of surgical-resection margins of gastric cancer by mass-spectrometric imaging", Proc Nail Acad Sci U S A, 111(7): 2436-2441 (Feb. 18, 2014).

(56) References Cited

OTHER PUBLICATIONS

Eberlin et al., "Cholesterol sulfate imaging in human prostate cancer tissue by desorption electrospray ionization mass spectrometry", Analytical Chemistry, 2010, 82(9): 3430-3434.
Dill et al. "Multivariate statistical differentiation of renal cell carcinomas based on lipidomic analysis by ambient ionization imaging mass spectrometry", Anal Bioanal Chem, 2010, 398(7-8): 2969-2978.
Dill et al., "Multivariate statistical identification of human bladder carcinomas using ambient ionization imaging mass spectrometry", Chemistry, 2011, 17(10): 2897-2902.
Santagata et al., Intraoperative mass spectrometry mapping of an onco-metabolite to guide brain tumor surgery, Proc Natl Acad Sci U S A, 111(30): 11121-11126 (Jul. 29, 2014).
Dill et al., "Lipid profiles of canine invasive transitional cell carcinoma of the urinary bladder and adjacent normal tissue by desorption electrospray ionization imaging mass spectrometry", Analytical Chemistry, 2009, 81(21): 8758-8764.
Dill et al., "Mass spectrometric imaging of lipids using desorption electrospray ionization", J Chromatogr B Analyt Technol Biomed Life Sci, 2009, 877(26): 2883-2889.
Calligaris et al., "Molecular typing of meningiomas by desorption electrospray ionization mass spectrometry maging for surgical decision-making", International Journal of Mass Spectrometry, 377: 690-698 (Mar. 31, 2014; published Feb. 1, 2015).
Eberlin et al., "Nondestructive, histologically compatible tissue imaging by desorption electrospray ionization mass spectrometry", Chembiochem, 2011, 12(14): 2129-2132.
Itata et al., "Contrast Agent Mass Spectrometry Imaging Reveals Tumour Heterogeneity", Anal Chem, Aug. 2015, 87(15): 7683-7689.
Alali et al., "Optimization of rapid Mueller matrix imaging of turbid media using four photoelastic modulators without mechanically moving parts", Opt Eng, 2013, 52(10): 103114-1 to 103114-8.
Rodriguez-Brenes et al., "Minimizing the risk of cancer: tissue architecture and cellular replication limits", J. R. Soc. Interface, 2013, 10(86): 20130410 (pp. 1-12).
Pierangelo et al., "Polarimetric imaging of uterine cervix: a case study", Opt. Express, 2013, 21(12): 14120-14130.
Antonelli et al., "Mueller matrix imaging of human colon tissue for cancer diagnostics: how Monte Carlo modeling can help in the interpretation of experimental data", Opt. Express, 2010, 18(1): 10200-10208.
Schäfer et al., "In vivo, in situ tissue analysis using rapid evaporative ionization mass spectrometry", Angew Chem Int Ed Engl, 2009, 48(44): 8240-8242.
Côté et al., "Robust concentration determination of optically active molecules in turbid media with validated three-dimensional polarization sensitive Monte Carlo calculations", Opt. Express, 2005, 13(1): 148-163.
Calligaris et al., "Application of desorption electrospray ionization mass spectrometry imaging in breast cancer margin analysis", Proc Natl Acad Sci U S A, 111(42): 15184-15189 (Oct. 21, 2014).
Lu et al., "Interpretation of Mueller matrices based on polar decomposition", Journal of Optical Society of America A, 1996, 13(5): 1106-1113.
International Preliminary Report on Patentability dated Apr. 5, 2018 in corresponding International Patent Application No. PCT/CA2016/051112.
Ghosh et al., "Influence of the order of the constituent basis matrices on the Mueller matrix decomposition-derived polarization parameters in complex turbid media such as biological tissues", Opt. Comm., 2010, 283(6): 1200-1208.
Alali et al., "Assessment of local structural disorders of the bladder wall in partial bladder outlet obstruction using polarized light imaging", Biomed. Opt. Express, 2013 (published Jan. 27, 2014), 5(2): 621-629.
Azu et al., "What is an adequate margin for breast-conserving surgery? Surgeon attitudes and correlates", Annals of surgical oncology, 2010, 17(2): 558-563.

Bhatti et al., "Safe negative margin width in breast conservative therapy: results from a population with a high percentage of negative prognostic factors", World Journal of Surgery, 2014, 38(11): 2863-2870.
Ghosh et al., "Polarimetry in turbid, birefringent, optically active media: A Monte Carlo study of Mueller matrix decomposition in the backscattering geometry", Appl. Phys., 2009, 105(10): 102023-1 to 102023-8.
Ghosh et al., "Mueller matrix decomposition for polarized light assessment of biological tissues", Journal of Biophotonics, 2009, 2(3): 145-156.
Wood et al., "Polarization birefringence measurements for characterizing the myocardium, including healthy, Infarcted, and stem-cell-regenerated tissues", J. Biomed Opt., 2010, 15(4): 047009-1 to 047009-9.
Qiu et al., "Displaying 3D radiation dose on endoscopic video for therapeutic assessment and surgical guidance", Physics in Medicine and Biology, 2011, 57(20): 6601-6614.
Weersink et al., "Improving superficial target delineation in radiation therapy with endoscopic tracking and registration", Medical Physics, 2011, 38(12): 6458-6468.
Agar et al., "Development of Stereotactic Mass Spectrometry for Brain Tumor Surgery", Neurosurgery, 2011, 68(2): 280-290.
Morris et al., "Evaluation of pectoralis major muscle in patients with posterior breast tumors on breast MR images: early experience", Radiology, 2000, 214(1): 67-72.
McDonnell et al., "Imaging mass spectrometry", Mass Spectrum Rev, 2007, 26(4): 606-643.
Yang et al., "Accurate quantification of lipid species by electrospray ionization mass spectrometry—Meet a key challenge in lipidomics", Metabolites, 2011, 1(1): 21-40.
Aichler et al. "Spatially Resolved Quantification of Gadolinium (III)-Based Magnetic Resonance Agents in Tissue by Maldi Imaging Mass Spetrometry after In Vivo MRI", Angew. Chem. Int. Ed., 2015, 54(14): 4279-4283.
Kennedy et al., "Investigation of Optical Coherence Microelastography as a Method to Visualize Cancers in Human Breast Tissue", Cancer Res, 2015, 75(16): 3236-3245.
Tillner et al., "Investigation of the Impact of Desorption Electrospray Ionization Sprayer Geometry on its Performance in Imaging of Biological Tissue", Anal Chem, 2016, 88(9): 4808-4816.
Skraskova et al., "Enhanced capabilities for imaging gangliosides in murine brain with matrix-assisted laser desorption/ionization and desorption electrospray ionization mass spectrometry coupled to ion mobility separation", Methods, 2016, 104: 69-78.
Zou et al., "Ambient Mass Spectrometry Imaging with Picosecond Infrared Laser Ablation Electrospray Ionization (PIR-LAESI)", Anal Chem, 2015, 87(24): 12071-12079.
Tata et al., "Rapid Detection of Necrosis in Breast Cancer with Desorption ElectroSpray Ionization Mass Spectrometry", Scientific Reports, 2016, 6: 35374, pp. 1-10.
Guenther et al., "Spatially resolved metabolic phenotyping of breast cancer by desorption electrospray ionization mass spectrometry", Cancer Res, 2015, 75(9): 1828-1837.
Tata et al., "Wide-field tissue polarimetry allows efficient localized mass spectrometry imaging of biological tissues," Chemical Science, 2016, 7: 2162-2169.
Puri et al., "A method for accurate spatial registration of PET images and histopathology slices", EJNMMI Research, 2015, 5(1): 64, pp. 1-11.
Chamma et al., "Optically-tracked handheld fluorescence imaging platform for monitoring skin response in the management of soft tissue sarcoma", Journal of Biomedical Optics, Jul. 2015, 20(7): 076011-1 to 076011-9.
Olga et al., "Co-registered Topographical, Band Excitation Nanomechanical, and Mass Spectral Imaging Using a Combined Atomic Force Microscopy/Mass Spectrometry Platform", ACS Nano, 2015, 4(9):4260-4269.

\* cited by examiner

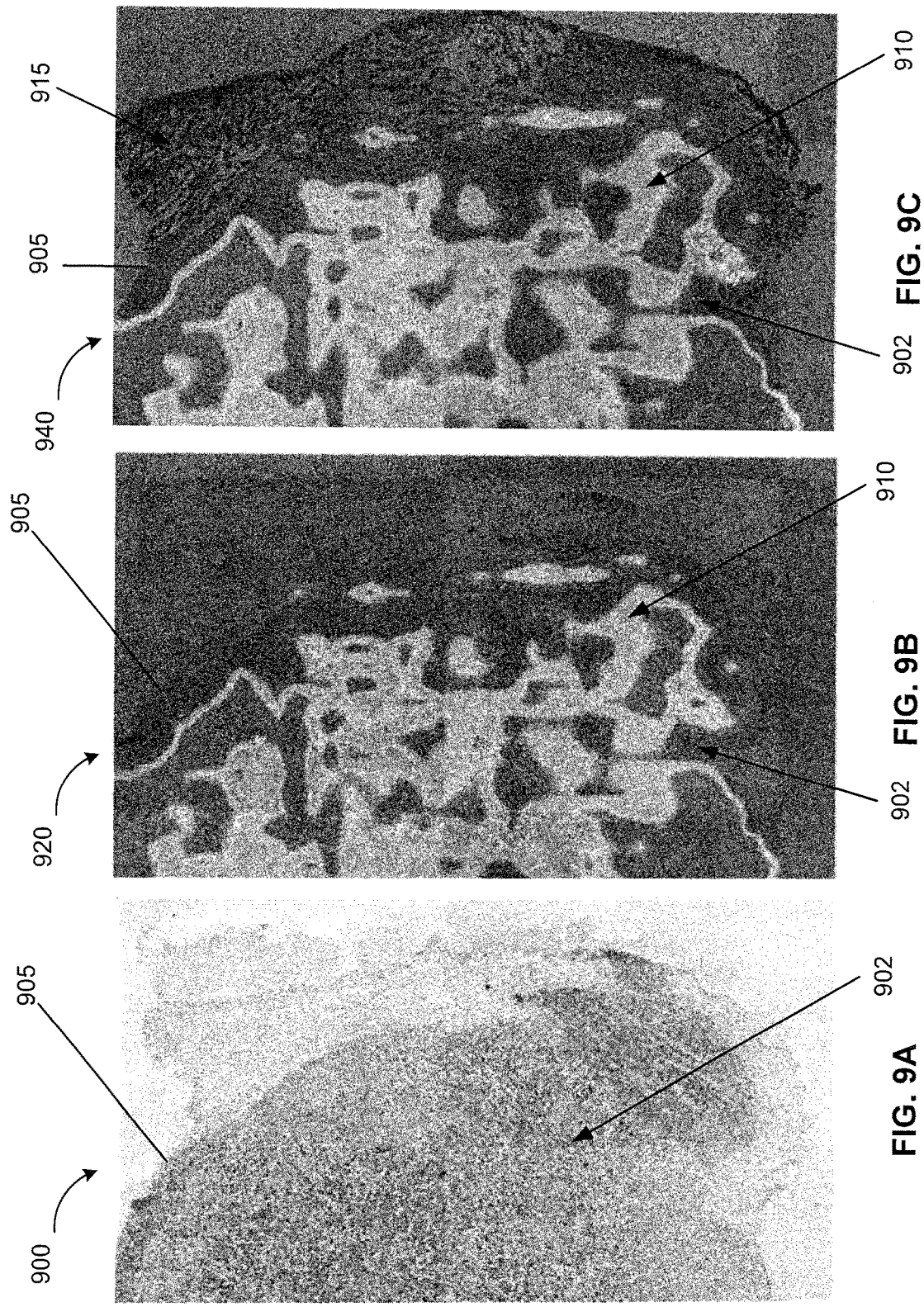

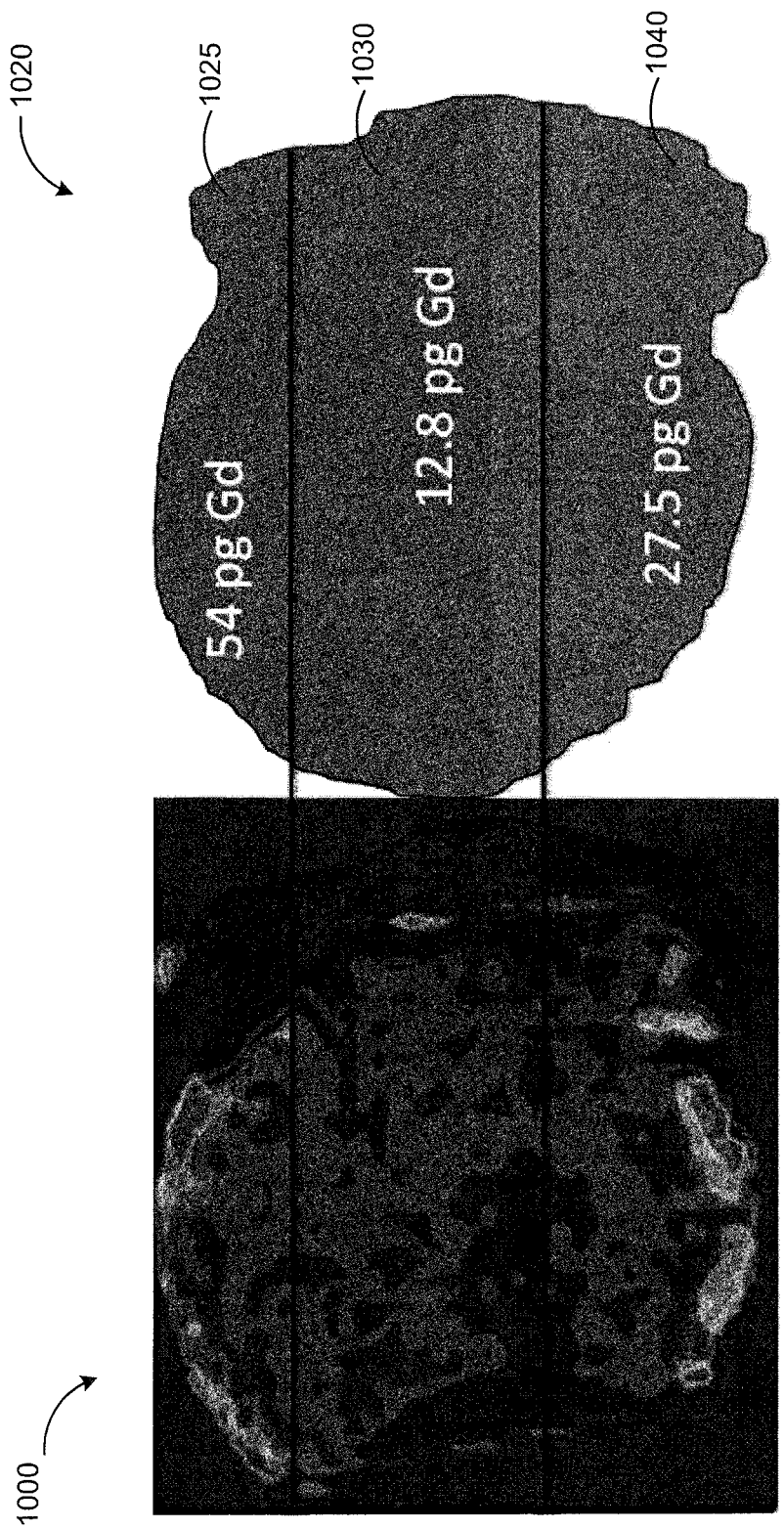

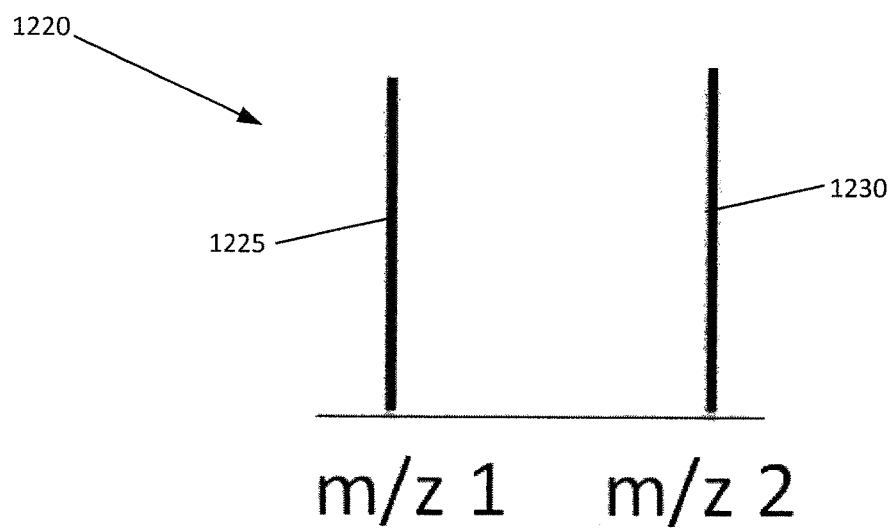
FIG. 12B
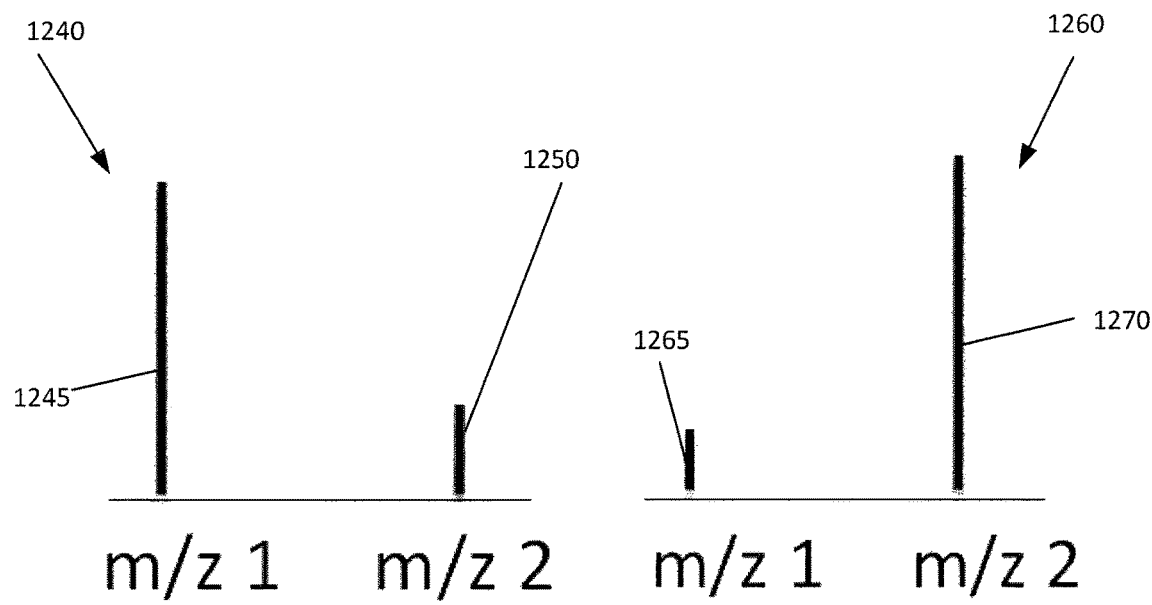
FIG. 12C  FIG. 12D

SYSTEM AND METHOD FOR ENHANCED MASS SPECTROMETRY IMAGING

CROSS-REFERENCE TO RELATED APPLICATION

This application claims the benefit and priority of U.S. Provisional Patent Application Ser. No. 62/088,964, filed on Dec. 8, 2014. The entire contents of such application are hereby incorporated by reference.

FIELD

The various embodiments described herein generally relate to a system and method for enhanced mass spectrometry imaging, in particular intraoperative mass spectrometry imaging using exogenous agents.

BACKGROUND

When operating on patients, surgeons often need to accurately identify a region of interest, such as a disease region or a tumor, as well as the boundary of that region of interest. In some cases, such as when excising a tumor, a surrounding margin of healthy tissue around the tumor will be removed to ensure that no diseased tissue remains. When the boundary of the disease region cannot be robustly identified, excess healthy tissue may be removed unnecessarily, potentially leading to disability for the patient.

While intraoperative pathology methods exist to reveal some disease regions, there can be significant difficulties in distinguishing the disease regions from surrounding tissues, such as fatty breast tissues for example. Intraoperative pathology methods may also take upwards of 30 minutes to identify healthy and diseased tissue regions, leading to delays during surgery. In some cases, these delays and insufficiently robust identification of the disease region can lead to patients having to undergo subsequent surgeries to ensure that the entire disease region has been removed.

Imaging Mass Spectrometry (IMS) is one technique to map the chemical content of biological tissues in a spatially resolved manner. Recent developments in IMS techniques have opened up the prospect of intraoperative molecular imaging to identify disease states of tissues for effective diagnosis. These methods identify the tissue disease states on the basis of spatially mapping endogenous disease markers.

Desorption by Electrospray Ionization (DESI) MS imaging has been used to identify and grade tumor regions into their respective subclasses on the basis of endogenous lipid profiles unique to each tumor class. The endogenous lipid profiles typically require strong cross-validation with conventional pathology methods. Accordingly, the success of DESI-MS imaging and other current ambient IMS technologies in identifying a diseased region is heavily tied to the availability of validated molecular markers for the disease in question.

SUMMARY OF VARIOUS EMBODIMENTS

In a broad aspect, at least one embodiment described herein provides a method of identifying a region of interest in tissue, the method comprising administering an exogenous agent to the tissue, the exogenous agent being capable of forming a by-product in the tissue; analyzing a sample based on the tissue using a high sensitivity platform comprising a mass spectrometer; determining a distribution, optionally quantitative, of the by-product of the exogenous agent within the tissue based on the analysis of the sample; and identifying the region of interest within the tissue based on the determined distribution of the by-product of the exogenous agent relative to tissue surrounding the region of interest.

In at least one embodiment, the determining act further comprises determining a distribution of the exogenous agent in addition to the by-product of the exogenous agent.

In at least one embodiment, prior to the analyzing act the method comprises acquiring the sample from the tissue after administration of the exogenous agent to the tissue; and transporting the sample to the mass spectrometer using a transfer line by applying a positive pressure on the transfer line at a first end proximate to the tissue.

In at least one embodiment, prior to the analyzing act the method comprises obtaining the sample from the tissue using an ex vivo sampling technique.

In at least one embodiment, the method further comprises selecting the agent from chelated metal containing agents and tumour specific metalloporphyrins, chelated metal containing agents being Gadolinium based, ion oxide based, iron-platinum based, manganese based, or chromium based.

In at least one embodiment, the method further comprises selecting the exogenous agent from at least one of a metallic element, a heavy atom, and an isotopic variant that is not endogenous to the tissue, a metabolic precursor, an isotopic variant of a metabolic precursor, a moiety of a metabolic precursor or a plurality of exogenous sub-agents.

In at least one embodiment, the method further comprises identifying a boundary of the region of interest based on the distribution of at least one of the exogenous agent, and the by-product of the exogenous agent relative to tissue surrounding the region of interest; and displaying an image of the tissue with the boundary marked.

In another broad aspect, at least one embodiment described herein provides a method of identifying a region of interest in tissue using mass spectrometry. The method includes administering an exogenous agent to the tissue, acquiring a sample based on the tissue after administration of the exogenous agent to the tissue, transporting the sample to a high sensitivity platform, analyzing the sample using the high sensitivity platform, determining a distribution of at least one of the exogenous agent and a by-product of the exogenous agent within the tissue based on the analysis of the sample, and identifying the region of interest based on the determined distribution.

In some embodiments, the high sensitivity platform can include a mass analyzer.

In some embodiments the high sensitivity platform can include at least one of an optical detection platform, a fluorescence detection platform and a Raman detector.

In some embodiments, the high sensitivity platform may include the at least one of an optical detection platform, a fluorescence detection platform and a Raman detector in tandem with a mass analyzer.

In some embodiments, the exogenous agent administered can include at least one of a metallic element, a heavy atom, and an isotopic variant. In some cases, the at least one isotopic variant can be an isotopic variant of an endogenous metabolic precursor. The method can include determining the distribution of a by-product of the isotopic variant of the endogenous metabolic precursor. In some embodiments, the isotopic variant is not endogenous.

In some embodiments, the exogenous agent can include at least one of a metabolic precursor and a moiety of a metabolic precursor. The method can include determining the distribution of a by-product of the at least one of the metabolic precursor and the moiety of a metabolic precursor.

In some embodiments, the exogenous agent can include a plurality of exogenous sub-agents. In some embodiments, the exogenous agent can be administered encapsulated in a lipidic structure such as a liposome.

In some embodiments, acquiring the sample can include desorbing the sample from the tissue. In some cases, the desorption can be performed using laser ablation vaporization, desorption electrospray ionization, or radio frequency ablation.

In some embodiments, the method includes ionizing the sample prior to analyzing the sample using the high sensitivity platform. In some cases, the sample can be ionized using plasma. In some cases, the sample can be ionized using inductively-coupled plasma. In some cases, the sample can be ionized using rapid evaporative ionization, or electrospray ionization.

In some embodiments, the high sensitivity platform can be configured to determine a distribution of the at least one of the exogenous agent and a by-product of the exogenous agent.

In some embodiments, the sample can be transported to the mass analyzer using a transfer line. In some cases, the method can further include applying a positive pressure on the transfer line at a first end proximate the tissue.

In some embodiments, the method further includes identifying a boundary of the region of interest based on the distribution of at least one of the exogenous agent, the isotopic variant, and the by-product of the exogenous agent. The method can further include displaying an image of the tissue with the boundary marked.

In some embodiments, the exogenous agent administered is selected such that the at least one of the exogenous and the by-product of the exogenous agent has at least one of a mass to charge ratio peak and an elemental mass peak that is not endogenous.

In some embodiments, the sample can be a tissue sample acquired from the tissue, an ablated tissue sample, an ablation plume, a liquefied tissue sample, an extraction of the exogenous agent, or an extraction of the by-product of the exogenous agent from the tissue. In some cases, the tissue sample can be an ex-vivo tissue sample.

In another broad aspect, at least one embodiment described herein provides a system for identifying a region of interest in tissue, the system comprising: a sampling unit configured to acquire a sample based on the tissue after administration of an exogenous agent to the tissue, the exogenous agent being capable of forming a by-product in the tissue; and a high sensitivity platform comprising a mass spectrometer, the high sensitivity platform being coupled to the sampling unit to analyze the sample, the high sensitivity platform being configured to determine a distribution, optionally quantitative, of a by-product of the exogenous agent within the tissue based on a spectral analysis of the sample to determine spectral peaks due to the by-product of the exogenous agent that are not endogenous to the tissue and to identify the region of interest based on the determined distribution of the by-product of the exogenous agent relative to tissue surrounding the region of interest.

In at least one embodiment, the high sensitivity platform is configured to determine a distribution of the exogenous agent in addition to the by-product of the exogenous agent based on a spectral analysis of the sample to determine spectral peaks due to the exogenous agent that are not endogenous to the tissue, and the exogenous agent and the by-product of the exogenous agent having at least one of a mass to charge ratio peak and an elemental mass peak that is not endogenous to the tissue.

In at least one embodiment, the system further comprises an agent administration component configured to administer an exogenous agent to the tissue prior to analysis by the mass spectrometer.

In at least one embodiment, the exogenous agent comprises a chelated metal containing agent or a tumour specific metalloporphyrins, the chelated metal containing agents being Gadolinium based, ion oxide based, iron-platinum based, manganese based, or chromium based.

In at least one embodiment, the exogenous agent used with the system is at least one of a metallic element, a heavy atom, and an isotopic variant that is not endogenous to the tissue, a metabolic precursor, an isotopic variant of a metabolic precursor, a moiety of a metabolic precursor or a plurality of exogenous sub-agents.

In at least one embodiment, the at least one isotopic variant comprises an isotopic variant of an endogenous metabolic precursor, and the high sensitivity platform is configured to determine the distribution of a by-product of the isotopic variant of the endogenous metabolic precursor.

In another broad aspect, at least one embodiment described herein provides a system for identifying a region of interest in tissue using mass spectrometry. The system can include an agent administration component, a sampling unit and a high sensitivity platform. The agent administration component can be configured to administer an exogenous agent to the tissue. The sampling unit can be configured to acquire a sample based on the tissue after administration of the exogenous agent to the tissue. The high sensitivity platform can be configured to analyze the sample, determine a distribution of at least one of the exogenous agent and a by-product of the exogenous agent within the tissue based on the analysis and identify the region of interest based on the distribution of the at least one of the exogenous agent and the by-product of the exogenous agent.

In some embodiments, the high sensitivity platform includes a mass analyzer.

In some embodiments, the high sensitivity platform includes at least one of an optical detection platform, a fluorescence detection platform and a Raman detector. The high sensitivity platform can include the least one of an optical detection platform, a fluorescence detection platform and a Raman detector in tandem with the mass analyzer.

In some embodiments, the agent administration component can be configured to administer an exogenous agent comprising at least one of a metallic element, a heavy atom, and an isotopic variant. In some cases, the isotopic variant comprises an isotopic variant of an endogenous metabolic precursor, and the high sensitivity platform can be configured to determine the distribution of the by-product of the isotopic variant of the endogenous metabolic precursor within the tissue. In some embodiments, the isotopic variant is not endogenous.

In some embodiments, the agent administration component can be configured to administer an exogenous agent comprising at least one of a metabolic precursor and a moiety of a metabolic precursor. The high sensitivity platform can be configured to determine the distribution of the by-product of the at least one of the metabolic precursor and the moiety of a metabolic precursor within the tissue.

In some embodiments, the agent administration component can be configured to administer an exogenous agent comprising a plurality of exogenous sub-agents. The agent administration component can be configured to administer the exogenous agent encapsulated in a lipidic structure, such as a liposome.

In some embodiments, the sampling unit includes at least one of a desorption component configured to desorb the sample from the tissue and a vaporization component configured to vaporize the sample from the tissue. The desorption component can be a laser ablation device.

In some embodiments, the sampling unit includes an ionization device configured to ionize the sample from the tissue. The ionization device can be a plasma ionization device such as an inductively-coupled plasma ionization device.

In some embodiments, the agent administration component can be configured to administer an exogenous agent including at least one metallic element. The high sensitivity platform can be a mass analyzer unit configured to determine a distribution of the at least one of the exogenous agent and the by-product of the exogenous agent in the tissue.

In some embodiments, the exogenous agent comprises at least one isotopic variant of the at least one metallic element and the mass analyzer unit can be further configured to determine a distribution of the isotopic variant in the tissue, and identify the region of interest based on the distribution of the isotopic variant.

In some embodiments, the system may also include a transportation unit including a transfer line that can couple the sampling unit and the mass analyzer unit. The transfer line can be configured to transport the acquired sample to the mass analyzer unit. In some cases, the transfer line can house either the desorption component or the vaporization component.

In some embodiments, at least one of the sampling unit and the transfer line comprises trackable markings. The high sensitivity platform can be configured to track the trackable markings to identify a location of the tissue where the sample was acquired.

In some embodiments, the transportation unit can be configured to apply a positive pressure on the transfer line at a first end of the transfer line, the first end proximate to the tissue region from which the sample is acquired.

In some embodiments, the system can also include a display device. The high sensitivity platform can be configured to identify a boundary of the region of interest based on the distribution of at least one of the exogenous agent, an isotopic variant, and the by-product of the exogenous agent, and the display device can display an image of the tissue with the boundary marked.

In some embodiments, the sample comprises a tissue sample from the tissue, an ablated tissue sample, an ablation plume, a liquefied tissue sample, an extraction of the exogenous agent, or an extraction of the by-product of the exogenous agent from the tissue. In some cases, the tissue sample is an ex-vivo tissue sample.

In some embodiments, the exogenous agent administered is selected such that the at least one of the exogenous and the by-product of the exogenous agent has at least one of a mass to charge ratio peak and an elemental mass peak that is not endogenous.

In another broad aspect, at least one embodiment described herein provides a use of a system for identifying a region of interest in tissue using mass spectrometry, wherein the system is defined herein.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described.

FIG. 9A is another diagram illustrating the boundary of a human breast cancer tumor.

FIG. 9B is a diagram illustrating an overlay of a DESI-MS image on PCK immunocytochemistry staining of the epithelial cells of the tissue shown in FIG. 9A.

FIG. 9C is a diagram illustrating an overlay of a DESI-MS image on Hematoxylin and Eosin (H&E) staining of the tissue shown in FIG. 9A.

FIG. 10A is a diagram illustrating the distribution of an exogenous agent in 3 areas of a breast cancer tumor.

FIG. 10B is a diagram illustrating a quantified distribution of the exogenous agent shown in FIG. 10A.

FIG. 12B is an example plot illustrating the peak ratios of an administered exogenous agent.

FIG. 12C is an example plot illustrating the peak ratios associated with the administered exogenous agent detected in the healthy region of FIG. 12A.

FIG. 12D is an example plot illustrating the peak ratios associated with the administered exogenous agent detected in the diseased region of FIG. 12A.

Figure 1:
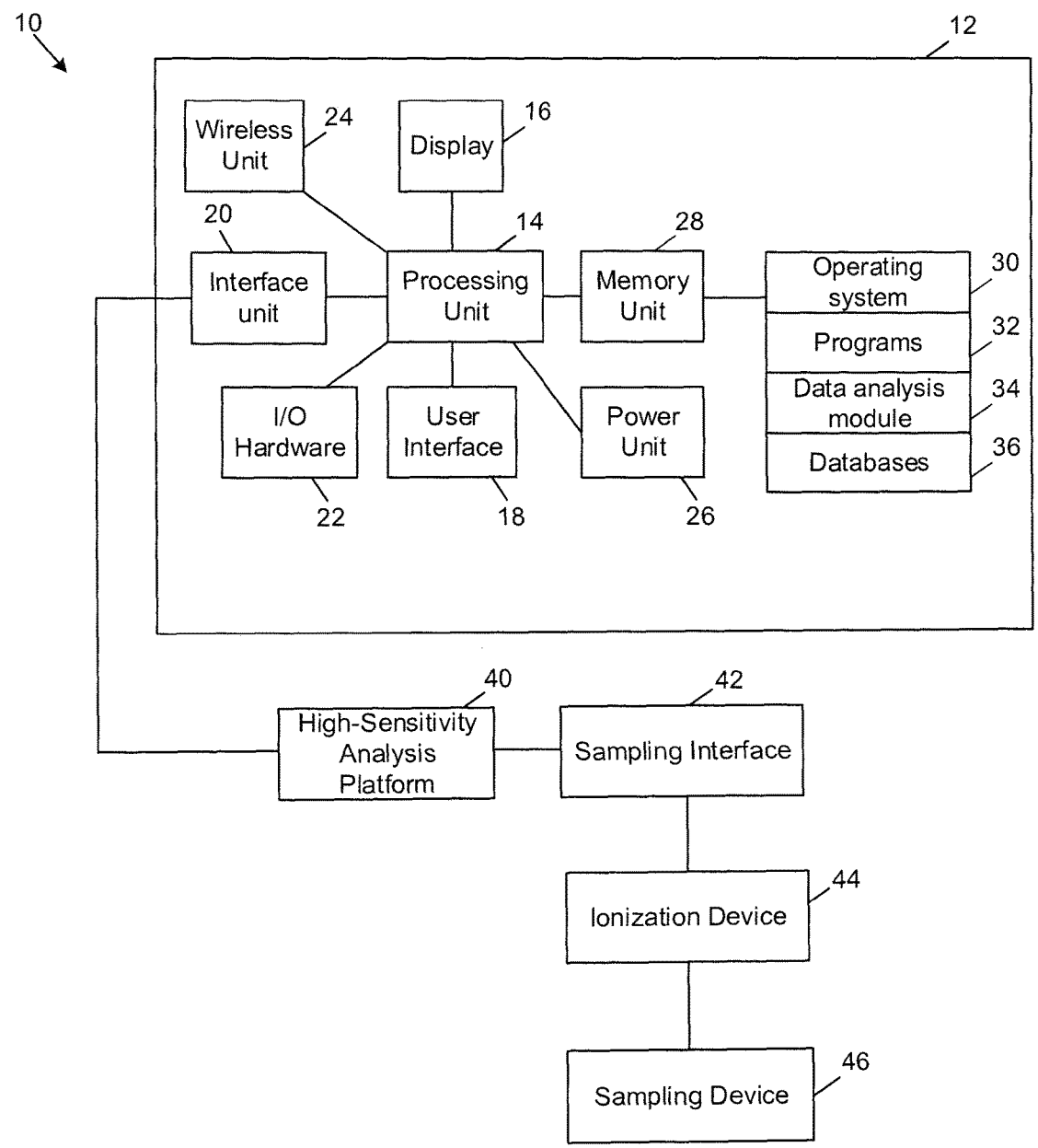
FIG. 1 is a block diagram of an example embodiment of a system that can be used for identifying a region of interest in tissue using mass spectrometry imaging.

Further aspects and features of the embodiments described herein will appear from the following description taken together with the accompanying drawings.

DETAILED DESCRIPTION OF THE EMBODIMENTS

Various apparatuses or methods will be described below to provide an example of an embodiment of the claimed subject matter. No embodiment described below limits any claimed subject matter and any claimed subject matter may cover methods or apparatuses that differ from those described below. The claimed subject matter is not limited to apparatuses or methods having all of the features of any one apparatus or methods described below or to features common to multiple or all of the apparatuses or methods described below. It is possible that an apparatus or methods described below is not an embodiment that is recited in any claimed subject matter. Any subject matter disclosed in an apparatus or methods described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

It should be noted that the term "exogenous agent" as used herein refers to any compound, chemical, drug, etc., such as, but not limited to, a contrast agent, which is capable of forming a by-product in the region of interest in the tissue and is identifiable from a sample based on the tissue using mass spectroscopy. The sample being based on the tissue means that the sample can be taken from the tissue, or it can be an altered version of the tissue due to the sampling process. Alternatively, the exogenous agent may be processed and metabolized in different regions of the tissue. The exogenous agent is typically not found naturally occurring in the body or is naturally occurring in the body at much smaller concentrations than when the exogenous agent is introduced to the body.

It should also be noted that the term "by-product" as used herein refers to a product or adduct formed in situ due to the degradation, ionization, complexation or otherwise transformation of the exogenous agent, and which is identifiable from the tissue or in the tissue using mass spectroscopy. For example, the exogenous agent may be ionized in situ to form an adduct such as, but not limited to, a salt, for example.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Conventionally identifying a diseased region is heavily tied to the availability of validated molecular markers for the disease in question. This has motivated many ex vivo studies to identify, validate and catalogue small molecule disease markers with utility in intraoperative IMS. While these IMS techniques provide promising avenues for exploration, wide adoption in the medical domain of small molecule mass spectrometry for identifying diseased regions has stalled mainly due to the strict requirement for biomarker knowledge.

Described herein are various example embodiments of a system and method that can be used for identifying a region of interest in a patient's tissue using mass spectrometry. The term patient as used herein is to be understood to refer to both human patients as well as animal patients. Although the systems and methods described herein may be used primarily with humans, they can also be applied to identify regions of interest in animal tissues as well. Examples of regions of interest include regions with different metabolic states, disease states, lesions, micro environments, regions of tissue heterogeneity such as stroma in a tumor, areas of necrosis or hypoxia, regions of inflammation and boundaries of tumors among others.

In particular, the systems and methods described herein can identify a region of interest in tissue based on the distribution of an exogenous agent within the tissue. In some embodiments, the region of interest may be identified based on the distribution of a by-product of the exogenous agent. For example, the by-product may be caused as a result of the processing and metabolism of the exogenous agent in different regions of the tissue, such as an adduct. In other embodiments, the region of interest may be identified based on the distribution of the by-product of the exogenous agent in addition to the exogenous agent. In other embodiments, the region of interest may be identified based on the distribution of the exogenous agent, such as in laser-based applications.

Embodiments of the systems and methods described herein may provide more accurate mapping of regions of interests compared to conventional techniques. Further, at least some of the embodiments described herein may allow regions of interests, such as tumors, to be mapped even without knowledge of endogenous markers. The size of such detected tumors are larger than the resolution of the sampling process (e.g. the laser focus, the DESI solvent spray focus, the size of the electrocautery probe, etc.) and the minimum sampling resolution (and therefore minimum detectable tumor size) ranges from about 20-50 microns to about one millimeter. In some cases, regions of interest can be identified by detecting regions of tissue having greater abundance of an administered exogenous agent, or showing an altered metabolism, absorption, processing, degradation, ionization, complexation or otherwise transformation of the exogenous agent compared to healthy tissue. Thus, regions of interest can be identified using a known administered exogenous agent even when an endogenous marker, such as a lipidic signature, is unknown for that particular region of interest.

Previous approaches to tumor type identification and tumor subclass grading rely heavily on the availability of validated molecular markers (endogenous markers) for the diseases being mapped. One such approach is described in detail in the patent application "System and method for identification of biological tissues" (WO 2010136887 A1) which identifies tissue samples based on "tissue-related" data that are endogenous to the tissue. This approach differs from the approach taken in the embodiments described herein as it identifies tissues based on endogenous markers, not exogenous agents, and is therefore severely hindered in adoption for widespread clinical use in instances where no validated markers exist for the disease in question. Here, the inventors have identified that the act of merely mapping a region of interest such as a tumor does not require knowledge of validated endogenous markers.

Some embodiments of the systems and methods described in accordance with the teachings herein are able to overcome the limitations of previous approaches using high sensitivity imaging of one or more exogenous agents introduced to a patient's tissue. For example, in accordance with the teachings herein, exogenous magnetic resonance (MR) contrast agents passively targeted to disease sites can be used with Ambient Desorption Electrospray Ionization Mass Spectrometry (DESI-MS) imaging to reveal disease sites without knowledge of endogenous markers for the disease. As discussed herein, these embodiments have been shown to reveal cancer regions in a mouse model of human breast tumors in test cases without invoking knowledge of lipidic markers for this disease. Other types of cancer regions that may be detected include brain cancer, bone cancer, prostate cancer, stomach cancer, kidney cancer, and lung cancer since these different cancers can be identified (e.g. can "light up") when using contrast agents (Xu G Z et al., "Comparison of FDG whole-body PET/CT and gadolinium-enhanced whole-body MRI for distant malignancies in patients with malignant tumors: a meta-analysis." Evidence-based Medical Center, The First Affiliated Hospital of Guangxi Medical University, Graduate School of Guangxi Medical University, Nanning, China; Ann Oncol. 2013; January 24(1): pp. 96-101.), and therefore the presence of such agents with cancer regions can be detected using mass spectrometry. Accordingly, any cancer that may be visualized using contrast enhanced medical imaging can be detected using the teachings herein.

The systems and methods described herein are not limited to using MR contrast agents as an exogenous agent, but can generally include all contrast agents used for medical imaging such as, but not limited to, small molecule exogenous agents, nanoparticle exogenous agents, as well as metabolic precursors, moieties of metabolic precursors (such as bifunctional molecules that may contain a metabolizable moiety and a tag for easy detection) and heavy atom contrast agents, for example. Similarly, the systems and methods described herein are not limited to using DESI-MS, and can use other forms of mass spectrometry technology such as, but not limited to, inductively-coupled plasma (ICP) mass spectrometry and matrix-assisted laser desorption ionization (MALDI) mass spectrometry imaging, for example.

In at least one embodiment, the exogenous agent is any agent capable of forming a by-product, wherein the by-product is identifiable using mass spectroscopy. In one embodiment, the exogenous agent is ionizable, thus forming an ionized by-product which is capable of forming a salt adduct with other ions present in situ. In a further embodiment, the exogenous agent is any agent containing a heavy atom, such as a transition metal, actinide, lanthanide, or other atom in periods 5, 6, or 7, such as iodine. In a further embodiment, the heavy atom is ionizable. For example, the exogenous agent is any metal-based agent, wherein the metal does not exist in the body, tissue and/or region of interest, or if the metal is present in the body, it is present at a significantly different concentration when the metal-based agent is administered. In another embodiment, the metal-based exogenous agent is a chelated metal agent (for example, a chelated gadolinium metal agent), an iron oxide containing agent, an iron-platinum containing agent, a manganese containing agent, a chromium containing agent, or tumour specific metalloporphyrins.

In one embodiment, the exogenous agent contains a heavy atom and is an MRI contrast agent, such as a metallic MRI contrast agent, or a CT (computerized tomography) contrast agent, such as an iodine-based CT contrast agent. In one embodiment, the MRI agent is gadoterate (Dotarem®), gadodiamide (Omniscan®), gadobenate (Multi Hance®), gadopentetate (Magnevist®, Magnegita®, Gado-MRT® ratiopharm), gadoteridol (ProHance®), gadoversetamide (OptiMARK®), gadoxetate (Primovist®), gadobutrol (Gadovist®), gadoterate (Dotarem®), gadodiamide (Omniscan®), gadobenate (Multi Hance®), gadopentetate (Magnevist®), gadoteridol (ProHance®), gadofosveset (Ablavar®), gadoversetamide (Opti MARK®), gadoxetate (Eovist®), gadobutrol (Gadavist®), Feridex I.V. (also known as Endorem® and ferumoxides), Resovist (also known as Cliavist®), Sinerem® (Combidex®), or Lumirem® (Gastromark®). In one embodiment, the iodine-based CT agent is diatrizoate, metrizoate, ioxaglate, iopamidol, or iohexol.

In one embodiment, the exogenous agent is gadoteridol. In another embodiment, the exogenous agent is gadoteridol which is ionizable in situ, and is capable of forming salt adduct based on the presence of various cations in the region of interest in the tissue. For example, the salt adduct is gadoteridol-$Na^+$ or gadoteridol-$K^+$.

In some embodiments, the exogenous agent can be in an ionized state on their own. In other embodiments, the exogenous agent can become ionized in the body after administration. In other embodiments, the exogenous agent can be ionized by using an ionization source before entry into a mass spectrometer. This latter ionization can take place either on the tissue surface during sampling for the mass spectrometer or after transport of a tissue plume to the entrance of the mass spectrometer (i.e. the ionization source can be placed anywhere along a transfer line between the tissue surface and the entrance of the mass spectrometer).

The embodiments described herein may be used to provide a new platform for accelerated intraoperative identification of tumor sites and other regions of interest in the absence of known markers. Furthermore, the highly multiplexed nature of mass spectrometry imaging may further simplify the disease identification process using a simple peak ratio test between metabolic or catabolic byproducts of exogenous agents differentially absorbed to, or metabolized by, the diseased tissues. In some cases, the peak ratio test can be used to determine a relative abundance of one or more exogenous sub-agents or by-products of the exogenous agent in a sample acquired from the tissue.

At least some of the embodiments of the systems and methods described herein may also provide the capability to perform quantitative mapping of regions of interest in tissue. In these cases, quantitative mass spectrometry can be used to determine a quantitative (or absolute) abundance of an administered exogenous agent or by-product of the administered exogenous agent. This may provide more robust identification of regions of interest and the boundaries of the regions of interest. This approach may also provide more accurate boundary assessment with exogenous agents that do not possess 100% targeting specificity, and are thus present in the tissues surrounding the region of interest, albeit to a lesser extent.

In one embodiment, the exogenous agents are administered intravenously as a solution, or alternatively, the agents are encapsulated inside liposomes or porphysomes and subsequently administered intravenously.

Administering exogenous agents that contain metallic elements along with the detection of these agents by Inductively Coupled Plasma Mass Spectrometry (ICP-MS), particularly in a spatially resolved manner, may provide a more robust assessment of the boundaries of regions of interest. The high tolerance to matrix effects of ICP-MS and quantitative ionization methods, such as photo ionization, may also provide more robust assessment of boundary regions. In some mass spectrometry methods, matrix effects arise from the influence of tissue constituent on the acquisition (including the desorption and the ionization steps) of exogenous agents. These matrix effects can impact the activity coefficients of the exogenous agent, leading to difficulties with non-quantitative detection of the exogenous agent using conventional mass spectrometry platforms. Non-quantitative imaging may have difficulty interpreting the intensity of some administered exogenous agents, such as contrast agents, because the intensity is affected by the properties of the tissue. As a result, a contrast agent may accumulate in a particular region, that is not the region of interest, but that non-quantitative imaging indicates is the region of interest. The robustness of quantitative MS, such as ICP-MS or gentle desorption as neutrals followed by quantitative ionization mass spectrometry in the face of these matrix effects enables the more robust identification and mapping of a region of interest. In ICP-MS, matrix material is obliterated by the high energy density of the plasma used to ionize the acquired sample thereby giving rise to a heavy atom signal associated with the administered exogenous agent in a matric independent manner. Nevertheless, many of the MS methods that are non-quantitative but which reliably produce signals associated with relative ion intensity can have adequate performance for identifying regions of interest.

Some embodiments in accordance with the teachings herein, such as those employing ICP-MS, may also use contrast agents in an injection dose far below what is required for conventional imaging modalities. As such, embodiments described herein may extend the benefit of intraoperative contrast-enhanced imaging of tumor boundaries to patients who may be currently excluded due to health concerns. These embodiments may also make the practice of tumor imaging with passive targeting of contrast agents safer for all patients since lower doses of those agents may be used to obtain acceptable imaging results.

The metallic elements contained in various exogenous agents used in the systems and methods herein are likely to survive the forces of laser ablation or electrocautery (which is used in the most commonly used scalpels in the operating rooms that offer cutting and restores homeostatis at the same time) and persist in the plume of electrocauterized tumors being resected. Accordingly, at least some embodiments of the systems and methods described in accordance with the teachings herein provide an intraoperative platform that may facilitate tumor resections on the basis of mass spectrometry imaging of exogenous agents (e.g. small molecule medical imaging contrast agents) or by-products in the exogenous agents present in the laser ablation (or electrocautery) plume of targeted tumors being resected.

Various ablation devices can be used with the systems and methods described herein, and the ablation devices can be operated in a variety of modes and with different parameters. For example, laser ablation can be performed using either a cauterizing or non-cauterizing laser operating in a variety of modes, wavelengths, pulse durations and average power values. In some cases, a laser ablation device that allows ablation in the absence of significant damage to the tissue can be used. Other ablation devices such as ultrasonic ablation devices, RF ablation devices and electrocautery devices can also be used.

In one particular embodiment, a platform is provided that comprises a transfer line (e.g. a suction-tube) coupling a high sensitivity analysis unit (e.g. MS or ICP-MS) with any of a variety of surgical laser scalpels or electrocautery blades, to provide intraoperative detection of exogenous agents that allows near real time assessment of tumor boundaries and is therefore much faster than intraoperative histology assessment. In some cases, the transfer line may be a heated tube that can be either rigid or flexible depending on the embodiment. In some cases, the transfer line itself may house the illumination point of a surgical laser scalpel or a desorbing laser fiber.

In another particular embodiment, there is provided a system including a high sensitivity analysis unit (e.g. MS or ICP-MS) on standby in an operating room along with an appropriate interface to sample tissue material that allows the analysis unit to measure, or to quantitatively measure (in preferred embodiment), the amount of an exogenous agent that is present in a conventional biopsy or nanobiopsy volume excised from a tumor being resected. This embodiment may allow the distribution and abundance (qualitative or quantitative) of an administered exogenous agent or by-product of the administered exogenous agent in an acquired sample to be determined within seconds, which is much faster than is currently possible with intraoperative histology.

Generally, embodiments of the system described herein may include an agent administration component that is configured to administer an exogenous agent to the tissue. The agent administration component can be configured to administer the exogenous agent in a variety of ways such as topically, enterally or parenterally.

In some cases, the agent administration component can be configured to administer the exogenous agent directly to the tissue being analyzed prior to acquisition of a sample from the tissue. For example, the exogenous agent can be sprayed or deposited onto the tissue in areas where samples are to be acquired. Alternatively, the agent administration component can be configured to administer an exogenous agent to a patient such that the exogenous agent diffuses to the region of the tissue being sampled. For example, the agent administration component may administer an exogenous agent to a patient orally, by injection (including any of intravenous, intramuscular, and subcutaneous injection), and/or by inhalation.

A wide variety of exogenous agents can be used with embodiments of the agent administration components described herein. Generally, the exogenous agent may be any chemical agent, drug, structure or functionality that is not a normal component of human or animal tissue, or one that contains an isotopic variant of an endogenous molecule. This can include, but is not limited to, various types of medical imaging contrast agents, drug molecules, metabolic precursors, moieties of metabolic precursors (such as bifunctional molecules that contain a metabolizable moiety and a tag for easy detection) functionalized molecules containing chelated metallic elements, nanoparticles or custom cocktails of mass tags.

In some cases, an exogenous agent may be administered that includes a plurality of exogenous sub-agents (i.e. a cocktail of exogenous agents) that undergo differential metabolism/absorption or processing at disease sites and other regions of interest so that these regions of interest can be identified by analyzing the distribution of the exogenous sub-agents that were administered. The term exogenous sub-agent is used herein to refer to the constituent components of an administered exogenous agent and may include an exogenous agent.

Embodiments of the system may further include a sampling unit configured to acquire a sample from the tissue. In different embodiments, the sampling unit can include various sub-units configured to acquire a sample of tissue for analysis. The sampling unit can be configured to acquire a sample in various forms, such as direct acquisition of a tissue sample, by collecting a plume of ablated tissue material from an electrocautery knife or a laser scalpel, and extraction of the exogenous agent or byproduct thereof from the tissue for example. In some cases, a plume of tissue material can be directly analyzed by the analysis platform while in other cases the plume of tissue material may be condensed prior to analysis. As a skilled reader will appreciate, in some cases tissue samples may require further processing such as freezing or sectioning for example, depending on the particular analysis platform implemented.

In some embodiments, the sampling unit may include a desorption component configured to desorb the sample from the tissue. For example, the desorption component may be a device such as, but not limited to, a laser ablation device, a liquid extraction device, an electrocautery device such as an electrocautery knife, an electrospraying device, an ultrasonic tissue atomizer, and a radio frequency ablation device among others.

Further, in at least some embodiments the sampling unit may include an ionization component configured to ionize the sample prior to analysis with the high sensitivity platform. For example, the ionization component may be a device such as, but not limited to, an electrospray ionization device, a laser ionization device, a matrix-assisted ionization device, a matrix-assisted laser desorption ionization device, an atmospheric pressure chemical ionization device, a photo ionization device, a laser based plasma source and an inductively-coupled plasma ionization device. In some cases, the sampling unit may not require an ionization component, for example where the administered exogenous agent includes charged particles, or becomes ionized as an adduct (i.e. by-product of the administered exogenous agent) in biological milieu.

In some cases, the sampling unit may also include an ex-vivo sampling unit that is able to acquire and secure an ex-vivo tissue sample from a patient, such as a biopsy or nano-biopsy sample of tissue that can be labelled by an exogenous agent. The ex-vivo sampling unit may include a platform for securing the tissue sample in place for analysis by a high sensitivity platform.

The system can also include a high sensitivity platform configured to analyze an acquired sample. In some embodiments, the high sensitivity (analysis) platform can include various types of mass analyzers used in mass spectrometry to determine a mass spectrum of the acquired sample. The high sensitivity platform may also include additional components, such as a processor, a display device and user controls depending on the particular embodiment. These additional components may further assist users in interacting with the system.

Generally, the high sensitivity platform can be any analysis platform that allows a more sensitive detection of the administered exogenous agent compared to conventional modality imagers currently used to image contrast agents or other exogenous contaminants (i.e. agents). The high sensitivity platform can be configured determine at least one of a mass to charge ratio and an elemental mass of at least one (expected) element in an acquired sample from the tissue. In some cases, the high sensitivity platform can be tuned to identify at least one of the presence (and also, therefore the absences) and the abundance of at least one of a mass to charge ratio associated with the administered exogenous agent (or a by-product of the administered exogenous agent) and an elemental mass associated with the administered exogenous agent (or a by-product of the administered exogenous agent). The high sensitivity platform can also be configured to detect an administered exogenous agent at per tissue pixel amounts, lower than, or consistent with the level required for conventional imaging modalities.

In some cases, the high sensitivity platform can include one or more of optical detection, fluorescence detection, Raman detection, stimulated or unstimulated Raman spectroscopy of exogenous agents targeted to tissues of expected regions of interest, Raman spectroscopy of desorbed exogenous material in a gas phase. In some cases, these detection methods can be used solely, while in preferred embodiments they may be used in tandem with mass spectrometry platforms.

In some cases, using additional analysis platforms in tandem may facilitate faster identification of regions of interest. For example, using a fluorescence detection platform, a fluorescent marker may reveal a potential region of interest to guide more detailed MS analysis of the region of interest. This may allow the high sensitivity analysis platform to be quickly targeted to a potential region of interest and thus enable rapid identification of the region of interest and the boundary of the region of interest.

The high sensitivity analysis platform may be configured to determine a distribution of an exogenous agent within the tissue based on the analysis of the sample acquired from the tissue. The high sensitivity platform can be configured to detect a smaller dose per pixel unit of the administered exogenous agent (or a by-product thereof) compared to conventional imaging modalities. The analysis platform may then identify a region of interest in the tissue based on the distribution of an exogenous agent, or a metabolic by-product of the exogenous agent. Regions of interest such as, but not limited to, tumors and other disease sites can be identified and mapped, even when endogenous markers are not yet known or validated.

Various exogenous agents can be used in the embodiments of systems and methods for identifying a region of interest in a sample as described herein. Typically, the exogenous agents will be agents that include chemical elements not found in the human body or chemical elements in ratios unnatural to those in the human body. In some embodiments, the exogenous agents can include chemical elements that are passively or actively targeted to, or absorbed, presented or metabolized differentially in diseased tissues versus healthy tissues.

In at least some cases, the exogenous agents used with the systems and methods described herein may also be limited to dose levels that are not considered toxic or harmful in humans. In at least some cases, the exogenous agents may be contrast agents developed for other imaging modalities. The use of a high sensitivity analysis platform may allow such contrast agents to be administered in doses that are lower than what is required in conventional imaging modalities. This may also allow contrast agents considered too toxic for use with other imaging modalities to be used safely at lower doses. Accordingly, contrast agents that identify regions of interest more effectively but may be considered too toxic at doses required for conventional imaging modalities may be used at lower, safe levels in embodiments of the systems and methods described herein.

In some cases, the exogenous agents may include at least one metallic element. This may allow regions of interest to be identified based on the distribution of the metallic element in the tissue. In some cases, the exogenous agents may include isotopic variants (e.g. variants of metallic isotopes or metabolic precursor isotopes). The distribution of isotope ratios of different isotopes can be used to identify regions of interest and the boundaries of regions of interest.

The use of exogenous agents may also allow regions of interest to be identified in a quantitative manner. At least some embodiments of the high sensitivity platform can be configured to determine a quantitative distribution of the exogenous agent or a by-product of the exogenous agent (or elements/isotopes thereof). For example, an inductively-coupled plasma mass spectrometry (ICP-MS) system may be used to determine a quantitative distribution of the exogenous agent. This may allow for a more precise and clear identification of regions of interest and the boundaries of the regions of interest. Such embodiments may provide more accurate boundary assessment with exogenous agents that do not possess 100% targeting specificity, and are also present in the tissues surrounding the regions of interest, albeit to a lesser extent.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, $C^{++}$ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Referring now to FIG. 1, shown therein is a block diagram of an example embodiment of a system 10 that can be used to identify a region of interest in a patient's tissue. The system 10 includes an operator unit 12, a high sensitivity analysis platform 40, a sampling interface 42, an ionization device 44 and a sampling device 46. The system 10 is provided as an example and there can be other embodiments of the system 10 with different components or a different configuration of the components described herein. For example, the system 10 can also include an agent administration component. The system 10 further includes several power supplies (not all shown) connected to various components of the system 10 for providing power thereto as is commonly known to those skilled in the art.

In general, a user may interact with the operator unit 12 and the sampling device 46 to acquire samples from the tissue, such as ex-vivo tissue samples from a patient or a plume of ablated tissue material, and then perform analysis and further data analysis (such as mass spectrometry) to identify a region of interest in the tissue. In some cases, the operator unit 12 and the analysis platform 40 may be combined as a high sensitivity analysis platform that is able to perform mass spectrometry analysis and further data analysis on a sample acquired from the tissue.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, a data analysis module 34, and one or more databases 36. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power depending on the configuration, purposes and requirements of the system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet, Local Area Network (LAN), Ethernet, Firewire, modem or digital subscriber line connection. Various combinations of these elements can be incorporated within the interface unit 20.

The I/O hardware 22 is optional and can include, but is not limited to, at least one of a microphone, a speaker, a display device and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data such as mass spectrometry data from the analysis platform 40, viewing and manipulating data, adjusting parameters related to data analysis as well as sending messages as the case may be.

In some cases, the acquired data may be preprocessed by the analysis platform 40 and transferred to the operator unit 12 through interface unit 20. The preprocessing may include standard signal processing techniques such as, but not limited to, at least one of amplification, filtering and de-noising (e.g. averaging) using parameters that depend on the particular signals of interest that are acquired. The interface unit 20 may be a multichannel data interface coupling the analysis platform 40 to the operator unit 12.

The data analysis module 34 processes the data that is recorded by the analysis platform 40 in order to identify the location of a region of interest in at least one image of the tissue region from which the sample(s) being processed were acquired. The data analysis module 34 is typically implemented using software, but there may be instances in which they are implemented using FPGA or application specific circuitry.

The databases 36 can be used to store data for the system 10 such as system settings, parameter values, and calibration data. The databases 36 can also store other information required for the operation of the programs 32 or the operating system 30 such as dynamically linked libraries and the like.

The operator unit 12 comprises at least one interface that the processing unit 14 communicates with in order to receive or send information. This interface can be the user interface 18, the interface unit 20 or the wireless unit 24. For instance, the exogenous agent whose distribution is being analyzed in a particular implementation of the system 10 may be inputted by a user through the user interface 18 or this information may be received through the interface unit 20 from a computing device. The processing unit 14 can communicate with either one of these interfaces as well as the display 16 or the I/O hardware 22 in order to output information related to the distribution of exogenous agent, identification of tumor locations and tumor boundary mapping. In addition, users of the operator unit 12 can communicate information across a network connection to a remote system for storage and/or further analysis in some embodiments. This communication may also include email communication.

The user can also use the operator unit 12 to input information needed for system parameters that are needed for proper operation of the system 10 such as calibration information and other system operating parameters as is known by those skilled in the art. Data that are obtained from tests, as well as parameters used for operation of the system 10, may be stored in the memory unit 28. The stored data may include raw acquired data, preprocessed acquired data as well as processed tumor location and tumor mapping data.

The analysis platform 40 comprises hardware and circuitry that is used to determine the distribution of an exogenous agent or a by-product of the exogenous agent in an acquired sample from the tissue. For example, the analysis platform 40 may be a mass analyzer that is configured to determine the mass-to-charge ratio and abundance of gas-phase ions in the acquired sample. In various embodiments, the analysis platform 40 may be implemented using a mass analyzer, a wide range scanner, or an application specific compact footprint limited mass range analyzer. In some cases, the analysis platform may also include at least one of an optical detection platform, a fluorescence detection platform and a Raman detector.

The sampling device 46 comprises hardware and circuitry that can be used to acquire a sample from a patient's tissue. In various embodiments, the sampling device 46 may be any one of a plurality of devices that can be used for desorbing samples from a patient's tissue, such as during a tumor rescission. For example, the sampling device 46 may be one of a laser ablation device, a liquid extraction device, an electrocautery device such as an electrocautery knife, an electrospraying device, an ultrasonic tissue atomizer, a radio frequency ablation device, and a plasma knife among others. The sampling device 46 may also include various types of sampling tools and equipment used to acquire and secure a biopsy or nano-biopsy sample for analysis by the analysis platform 40. The sampling device 46 may also include a small needle that can be used to acquire tissue samples for analysis in an ex-vivo analysis platform.

The ionization device 44 comprises hardware and circuitry that can be used to ionize an acquired sample prior to analysis by the analysis platform 40. In various embodiments, the ionization device 44 can be any one of a variety of ionization devices used in mass spectrometry applications. For example, the ionization device 44 can be one of an electrospray ionization device, a laser ionization device, a matrix-assisted ionization device, a matrix-assisted laser desorption ionization device, an atmospheric pressure chemical ionization device, a photo ionization device, rapid evaporative ionization device, and an inductively-coupled plasma or laser plasma ionization device among others.

In some cases, the ionization device 44 may be co-located with the sampling device 46 and may ionize the acquired sample at the source. In some cases, the sampling device 46 and the ionization device 44 may be combined, for example using desorption electrospray ionization. In other cases, the ionization device 44 may be located closer to the analysis platform 40 and may ionize an acquired sample after transportation to (or near to) the analysis platform 40. Alternatively, in some cases, the system 10 may not include an ionization device 44, for example where the exogenous agent being administered is charged, or becomes charged by virtue of adducts formed with endogenous tissue material.

The sampling interface unit 42 can be used to transport an acquired sample to the high sensitivity platform and/or support a sample for analysis with the high sensitivity platform. In some cases the sampling interface unit 42 can be a transportation unit that may include a transfer line coupling the sampling device 46 (and optionally the ionization device 44) to the analysis platform 40. The transfer line can be configured to transport an acquired sample to the high sensitivity platform.

For example, the transfer line may use the suction provided by the analysis platform 40 to transport a sample acquired by the sampling device 46 to the analysis platform 40. Alternatively, in some cases, the transfer line may use an additional pump to provide suction by introducing negative pressure at the analysis platform side of the transfer line to pull the sample from the sampling device 46 to the analysis platform 40.

In some cases, the transfer line may be a heated tube. In various embodiments the transfer line can be rigid or flexible. In some cases, the transfer line may also house the illumination point of the ionization device 44. For example, the transfer line can house a laser fiber that can be used to desorb a sample from the tissue. In some cases, an ionization device 44 can be located at a first end of the transfer line proximate the tissue, while in other cases the ionization device can be located at a second end of the transfer line, closer to the analysis unit 40.

In various embodiments, using an ICP-MS system the ionization device 44 may use inductively-coupled plasma to ionize an acquired sample. In one such embodiment, the sampling interface unit 42 may also include a transfer line coupling the sampling device 46 and the mass analyzer of the ICP-MS system. The sampling interface unit 42 can be configured to apply a positive pressure on the transfer line at a first end of the transfer line, the first end being proximate to the tissue being sampled. This may allow the acquired sample to be transported to the mass analyzer more rapidly in embodiments employing the suction of the mass analyzer unit.

In some cases, the transfer line may also include tracking markers. The analysis platform 40 can be configured to identify a location of the tracking markers to identify the location of the first end of the transfer line proximate the location of the sample being acquired. This can be used to track the location from which the sample was acquired, to be used when determining a distribution of the exogenous agent or by-product and identifying the region of interest and the boundary thereof.

Figure 2:
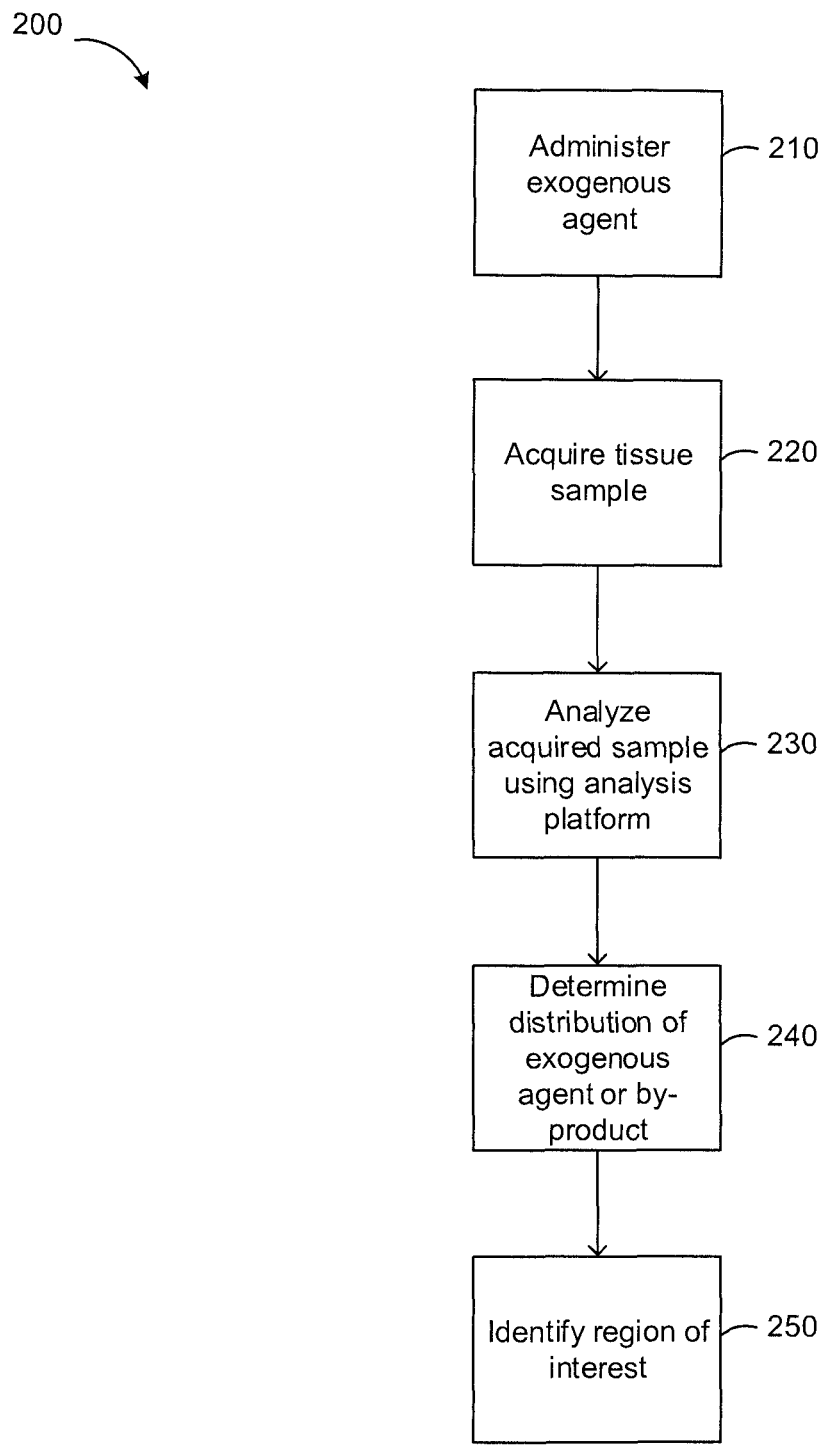
FIG. 2 is a flowchart of an example embodiment of a method that can be used to identify a region of interest in tissue using mass spectrometry.

Referring now to FIG. 2, shown therein is a flowchart 200 of an example embodiment of a method for identifying a region of interest in tissue using mass spectrometry.

At 210, an exogenous agent is administered to the patient. The exogenous agent can be administered in various ways, such as direct administration (e.g. depositing or spraying), oral ingestion, injection, and inhalation of the exogenous agent, for example. In some cases, the exogenous agent can be administered directly to an area of tissue expected to include the region of interest. In other cases the exogenous agent may be administered to the patient elsewhere and allowed to diffuse to the tissue that will be sampled, for example when administered orally, by injection or by inhalation. The exogenous agent can also be administered to the tissue in various ways including labelling by spraying or depositing (in vivo or ex vivo).

Generally, the exogenous agent administered may be any chemical agent, drug, structure or functionality that is not a normal component of human or animal tissue, or one that contains an isotopic variant of an endogenous molecule. In some embodiments, the exogenous agent can be any contrast agent already used and approved for use. In some cases, the administered exogenous agent can also include at least one metallic element, a metabolic precursor, an isotopic variant, or at least one heavy atom for example. In some cases, the exogenous agent can be administered in a known clinically relevant dose, while in some cases the dose may be lower than compared to what is required in a conventional imaging modality. A lower dose can be used in some cases due to the high sensitivity analysis platform 40 used to analyze the samples acquired from the tissue.

In some cases, a custom designed exogenous agent can be used that includes a plurality of exogenous sub-agents.

Using a plurality of exogenous sub-agents can enable a region of interest to be identified based on a distribution of each the plurality of exogenous sub-agents (or by-products thereof). This may provide more than one identifying mass to charge ratio peak or elemental mass peak during analysis by the high sensitivity platform 40. Areas where the peaks are coincident for the exogenous sub-agents (or by-products) can then be used to identify the region of interest.

The plurality of exogenous sub-agents can be administered in a variety of ways. For example, each of the exogenous sub-agents may be administered simultaneously or encapsulated in a carrier vehicle. In some cases, the carrier vehicle can be a lipidic structure such as a liposome for example for these exogenous sub-agents and the exogenous agents described herein, as well as existing imaging contrast agents described herein and any combination thereof, and all agents being developed for use with MRI, CT or Fluorescence imaging. This can allow a plurality of exogenous sub-agents to be administered as an exogenous agent in a mixture that facilitates efficient detection with a high sensitivity analysis platform such as mass spectrometry.

At 220, a sample from the tissue is acquired, for example using the sampling device 46. In some cases, the sample may be acquired prior to administering an exogenous agent, for example when the exogenous agent is administered to a tissue sample ex-vivo. In other cases the sample can be acquired after administration of an exogenous agent, using the administration methods described herein such as in vivo labelling, oral ingestion or intravenous injection.

The sample can be acquired in a variety of ways, such as by direct desorption of in vivo tissue or from ex vivo biopsied samples. Examples of sampling techniques for in vivo tissues include, but are not limited to, laser ablation vaporization, liquid extraction, capture of electrocautery plumes, radio frequency ablation, ultrasonic ablation, and DESI etc. Further, the sample can be acquired in a variety of forms, such as a sample of the tissue itself, as a plume from an electrocautery knife or a laser ablation device, or by extracting the exogenous agent or a by-product of the exogenous agent from the tissue (without acquiring a sample of the tissue itself) such as by using liquid extraction for example.

In some cases, the sample may also be ionized when the sample is acquired or after the sample is acquired, but before analysis. For example, the sample may be ionized using a plasma source such as inductively-coupled plasma. When a transfer line is used, the sample can be ionized prior to being transported towards the analysis platform 40 or after transportation by the transfer line, but prior to analysis by the analysis platform 40. Other ionization methods may also be used depending on the particular embodiment of the ionization device 44 that is implemented. In some cases, ionization of an acquired sample may not be necessary, for example where the administered exogenous agent already comprises ions or has by-products that become ionized in the tissue.

At 230, the acquired sample is analyzed using a high sensitivity analysis platform. The analysis platform 40 may identify a mass spectrum of the elements in the acquired sample. The analysis platform 40 can identify the mass-to-charge ratio (and/or elemental mass) and abundance of gas-phase ions in the acquired sample. In some cases, two-dimensional spectrometry imaging may be used to determine the presence and/or abundance of elements having different mass-to-charge ratios. In some cases, the analysis platform 40 may be configured to determine a relative abundance of the ions present in the acquired sample. In other cases, the analysis platform can be configured to determine an absolute (i.e. quantitative) abundance of the ions present in the acquired sample.

Various types of high sensitivity analysis platforms can be used here, such as, but not limited to, mass analyzers, wide range scanners and application specific compact footprint limited mass range analyzers. In some cases, one or more of an optical detection platform, a fluorescence detection platform, a Raman detection platform, a stimulated or unstimulated Raman spectroscopy platform for spectroscopy of exogenous agents targeted to tissue types expected to be in a region of interest, and a Raman spectroscopy platform for spectroscopy of desorbed exogenous material in a gas phase. In some cases, these further detection platforms can be used solely, while in preferred embodiments they may be used in tandem with mass spectrometry analysis platforms mentioned above.

In some cases, the analysis platform 40 may identify a signal intensity of one or more mass to charge ratio peaks and/or elemental mass peaks. For example, the analysis platform 40 may identify the signal intensity of one or more mass to charge ratio peaks and/or elemental mass peaks associated with the administered exogenous agent or a by-product of the administered exogenous agent. In some cases, the signal intensity may reflect a relative abundance of ions, whereas in other cases the signal intensity may reflect a quantitative abundance of ions in the sample. In some cases, the analysis platform 40 can be tuned so that it only provides as an output the peaks for associated with the exogenous agent or its by-product.

In some cases, the acquired sample may be transported to the analysis platform 40 directly. For example, where the acquired sample is vaporized, desorbed and/or ionized in vivo the sample can be directly transported to the analysis platform 40 by a transfer line in the sampling interface 42. In some embodiments, the transfer line may transport the acquired sample using suction or a carrier gas. In some cases, the sampling interface 42 may also apply a positive pressure to the transfer line at the sample source to accelerate the transportation of the sample to the analysis platform.

In some cases, the acquired sample may be a tissue sample such as an ex vivo tissue sample or a small biopsy sample. In such cases, the acquired sample may be labelled and then provided to the analysis platform 40 for analysis. In other cases, the acquired sample can be captured liquefied tissue material or a condensed plume of ablated tissue material that can be provided to the analysis platform 40. In further cases, acquiring the sample may comprise extracting the exogenous agent or by-product of the exogenous agent from the tissue and providing it to the analysis platform 40 for analysis.

In some cases sample processing may also be performed in combination with analysis by the high sensitivity platform. For example, this may include the addition of a matrix, processing under ambient or vacuum conditions, taking a subsection of a tissue sample, freezing a tissue sample, and slicing a tissue sample.

In some cases, the analysis platform 40 can be selectively tuned to identify elements or isotope variants of the exogenous agent that was administered at 210. One example embodiment of a selectively tuned analysis platform 40 can be implemented using an ICP-MS tuned to the metal elements contained in a contrast agent that is used as the exogenous agent that is administered to the tissue.

At 240, the distribution of the exogenous agent or a by-product of the exogenous agent is determined. The analysis platform 40 or the data analysis module 34 can be configured to determine the distribution of the exogenous agents (or by-products) based on the analysis of the acquired sample performed at 230. The distribution may be represented as a spatially resolved molecular map of the tissue. The molecular map can be stored after being processed with software platforms to convert the spectra acquired during the analysis of the sample at 230 to spatial 2-D coordinate positions within the surface of the tissue. Each acquired sample may also have associated therewith a location marker indicating a position on the surface of the tissue where that sample was acquired.

For example, the distribution may represent different regions where elements having a mass-to-charge ratio corresponding to the exogenous agent (or by-product) are identified as being present. In some cases, the distribution of the exogenous agent may be determined quantitatively, for example by using an ICP-MS system. Quantitative analysis of the distribution of the exogenous agent may allow the relative abundance of the exogenous agent to be determined for each portion of the tissue from which samples were acquired and analyzed. In some cases, the distribution may be a distribution of the signal intensity of the one or more mass to charge ratio peaks and/or elemental mass peaks identified at 230. This distribution can be displayed by display 16 as a heat map and can be used to identify a boundary of the region of interest. This can further be used to indicate the region of interest to a surgeon to guide surgery to eliminate a disease region.

In some cases, the exogenous agent may comprise a plurality of isotopic variants. In such embodiments, the analysis platform 40 or the data analysis module 34 can be configured to determine the distribution and relative abundance of the different isotopes (e.g. isotopic variants of a metallic element or a metabolic precursor) or by-products of those isotopes in the acquired sample(s). That is, the presence of elements having the mass to charge ratio associated with each isotopic variant can be identified, and in some cases their absolute abundance in different tissue regions can be determined (e.g. using ICP-MS).

Determining the presence and/or abundance of one or more isotopic variants in tissue regions can be used to determine a distribution of the one or more isotopic variants in the sample(s) being analyzed. In some cases, regions indicating a higher abundance of one or more isotopic variants may indicate a region of interest where the one or more isotopes are targeted or differentially absorbed or metabolized by the region of interest. The distribution can also be used to identify boundaries of regions of interest, for example by identifying regions having relatively different abundance levels of a particular isotopic variant.

In some cases, the administered exogenous agent can include an isotopic variant of an endogenous metabolic precursor (i.e. the isotopic variant of the metabolic precursor in the exogenous agent is not endogenous). Using isotopic variants of metabolic precursors allows the exogenous agents to be distinguished from endogenous tissue metabolites. The distribution of the exogenous agent may indicate regions of differential uptake, metabolism, absorption and processing of the exogenous agent. In particular, such regions may be indicative of the region of the interest. Using isotopic variants that are not endogenous to the patient body may facilitate detection and unambiguous identification of the exogenous agent or by-product of the exogenous agent (as compared with endogenous molecules that constitute normal tissue chemistry) thereby facilitating a more accurate and robust identification of the region of interest.

In some cases, the distribution of the exogenous agent or by-product may be shown as a level of signal intensity detected in a particular region. This may be in the form of a mass spectrum, such as the mass spectrum plots shown in FIG. 5A. The distribution may also be shown in two-dimensions, for example with the regions where the exogenous agent was detected highlighted. This can be shown to a surgeon using the display unit 16. Distribution profiles can be overlaid with images showing the structure of the tissue being analyzed, such as the images shown in FIG. 7. In some cases, regions having a greater abundance of the exogenous agent may be identified in output images with brighter highlighting or using a color map. This may be used by a surgeon to quickly identify the boundaries of region of interest, for example when removing a tumor.

In some cases, an exogenous agent comprising a plurality of exogenous sub-agents can be administered to the tissue. The plurality of exogenous sub-agents can be identified in the sample and a distribution of each of the exogenous sub-agents can be determined using the systems and methods described herein. In some cases, an overlapping distribution can be determined indicating regions where the distribution of each of the exogenous sub-agents (or by-products of the exogenous sub-agents) is coincident. Identifying regions where the exogenous sub-agents (or by-products) are coincident may provide a more robust marker for a region of interest and the boundary of the region of interest.

At 250, a region of interest is identified based on the distribution of the exogenous agent or a by-product of the exogenous agent determined at 240. Identifying the region of interest based on the distribution of an exogenous agent may allow disease sites and other regions of interest to be identified even without validated markers for the region of the interest. In some cases, standard techniques can be used to identify the boundaries of a region of interest, such as principal component analysis and other statistical methods for example.

In at least some cases, a peak ratio test can be used to identify a region of interest and the boundaries of regions of interest. This may involve qualitative and/or quantitative comparison of the m/z (mass-to-charge-ratio) peaks of the exogenous agent administered to the tissues. The ratio of peaks may identify regions of interest where the administered exogenous agent is differentially absorbed or metabolized in tissues in the region of interest as compared to the surrounding tissue (e.g. healthy tissue vs. diseased tissue). In some cases, the exogenous agent administered can be chosen to optimize the differential absorption or metabolism of the exogenous agent (or a plurality of exogenous sub-agents). For example, the exogenous agent can be chosen so that the peaks corresponding to the exogenous agent and/or by-product are likely to be easily distinguishable from background tissue peaks.

Figure 12A:
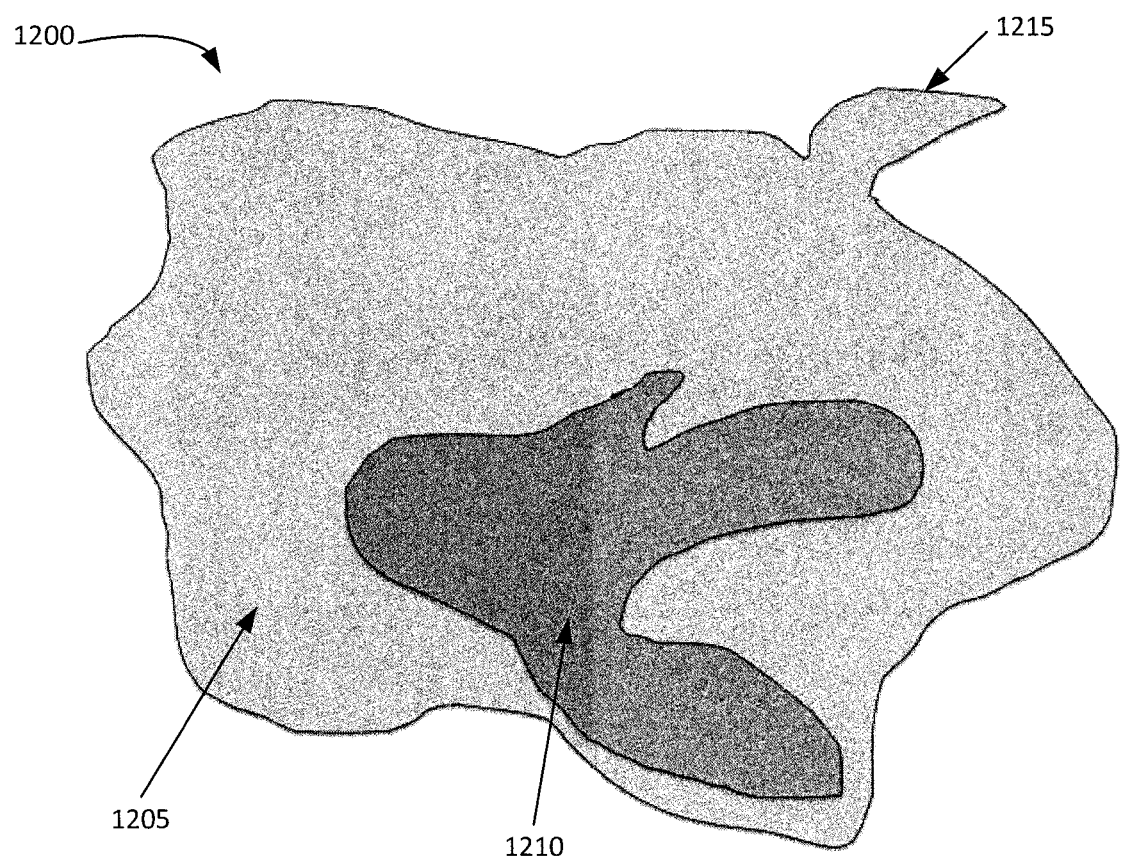
FIG. 12A is a diagram illustrating an example tissue region including a region of healthy tissue and a region of diseased tissue.

Referring now to FIG. 12A, shown therein is an illustration 1200 of a section of tissue having a healthy tissue region 1205 and a diseased tissue region 1210. In this case, the systems and methods described herein will typically be employed to identify the diseased tissue region 1210 as the region of interest. To do so, an exogenous agent can be administered to the tissue at administrating location 1215. The exogenous agent can be administered in various ways, as described above, including either direct administration to the tissue (e.g. spraying or depositing) or allowed to diffuse to the tissue regions after being administered indirectly (e.g. orally, by injection etc.).

Referring now to FIG. 12B, shown therein is a plot 1220 of the signal intensity of the peaks associated with exogenous sub-agents included in exogenous agent administered at 1215. The administered exogenous agent includes a first sub-agent having a mass to charge ratio m/z1 and a second sub-agent having a mass to charge ratio m/z2. As shown in plot 1220, the exogenous agent administered at 1215 includes a mixture of the first sub-agent and the second sub-agent at amounts that give rise to the signal intensity peaks shown in plot 1220. The first sub-agent peak 1225 and the second sub-agent peak 1230 indicate that the relative abundance of the first sub-agent and the second sub-agent are substantially the same in the exogenous agent administered.

Referring now to FIG. 12C, shown therein is a plot 1240 of the signal intensity peaks detected for the first sub-agent (peak 1245) and the second sub-agent (peak 1250) respectively in the healthy tissue region 1205. As plot 1240 shows the first sub-agent peak 1245 indicates a greater relative abundance of the first sub-agent in the healthy region 1205 as compared with the second sub-agent peak 1250, indicating a lower relative abundance of the second sub-agent.

Referring now to FIG. 12D, shown therein in a plot 1260 of the signal intensity peaks detected for the first sub-agent (peak 1265) and the second sub-agent (peak 1270) respectively in the diseased tissue region 1210. As plot 1260 shows, the first sub-agent peak 1265 indicates a lower relative abundance of the first sub-agent in the diseased region 1210 as compared with the second sub-agent peak 1270, indicating a lower relative abundance of the second sub-agent.

As shown in FIGS. 12C and 12D, the first sub-agent and the second sub-agent are metabolized differently within the healthy tissue region 1205 and the diseased tissue region 1210. The exogenous agent administered at 1215 can be selected such that the metabolism of the exogenous sub-agents administered can be known before detection. Accordingly, analysis of the ratio between the signal intensity peaks for the first sub-agent and the second sub-agent can be used to identify regions of the interest.

In some cases, depending of the high sensitivity platform used, the signal intensity peaks may reflect the relative abundance of each exogenous sub-agent in the samples, while in other cases the signal intensity peaks may reflect the absolute abundance of each exogenous sub-agent. In either case, a peak ratio test can be used to determine a relative abundance ratio between the two exogenous-sub agents.

In some cases, a more robust assessment of the boundaries of a region of interest can be determined using a quantitative distribution of the exogenous agent. For example, using ICP-MS to determine the quantitative abundance of the administered exogenous agent and/or isotopic variants of the exogenous agent may allow the boundaries of the region of the interest to be more clearly delineated as compared with qualitative detection of an exogenous agent. This may be particularly useful with exogenous agents that are not 100% targeted to the regions being mapped as the exogenous agents may be present in the tissue areas surrounding the region of interest, albeit less abundantly.

Some qualitative methods of determining the distribution of an exogenous agent may only indicate whether the exogenous agent is present. Thus, the boundaries of the regions of interest may be less well-defined as some tissues surrounding the region of interest may also be identified as having exogenous agent present. Using quantitative analysis methods, the relative abundance of an exogenous agent in different regions of a tissue can more clearly indicate the boundaries of a region of interest. For example, a tumor region may have a much higher abundance of the exogenous agent than the surrounding tissues, which will have exogenous present, but in much smaller quantities.

Furthermore, the analysis platform 40 can be configured to track the position on the surface of the tissue where each sample is acquired. In some cases, this can be done using trackable markings provided on the sampling device 46 or the transfer line.

By tracking the position of the acquired sample on the surface of the tissue, the distribution of the exogenous agent or by-product can be rapidly determined and used to identify the region of interest. The analysis platform 40 can dynamically average and scale/smooth the analysis results (e.g. the signal intensity of the mass to charge ratio peak or the elemental mass peak per pixel) from the analysis of each acquired sample to rapidly update and display the distribution of the exogenous agent on display 14. A boundary of the region of interest can thus be identified more rapidly and a surgeon can re-plan a resection more rapidly. This can reduce the need to take extremely wide margins that risk profound disability by removing too much of the healthy tissue. As discussed below with reference to FIGS. 11A-11C, quantitative detection of the distribution of the exogenous agent can provide a more accurate and robust indication of the boundaries of regions of interest and can further facilitate the re-planning of a resection.

Figure 11A:
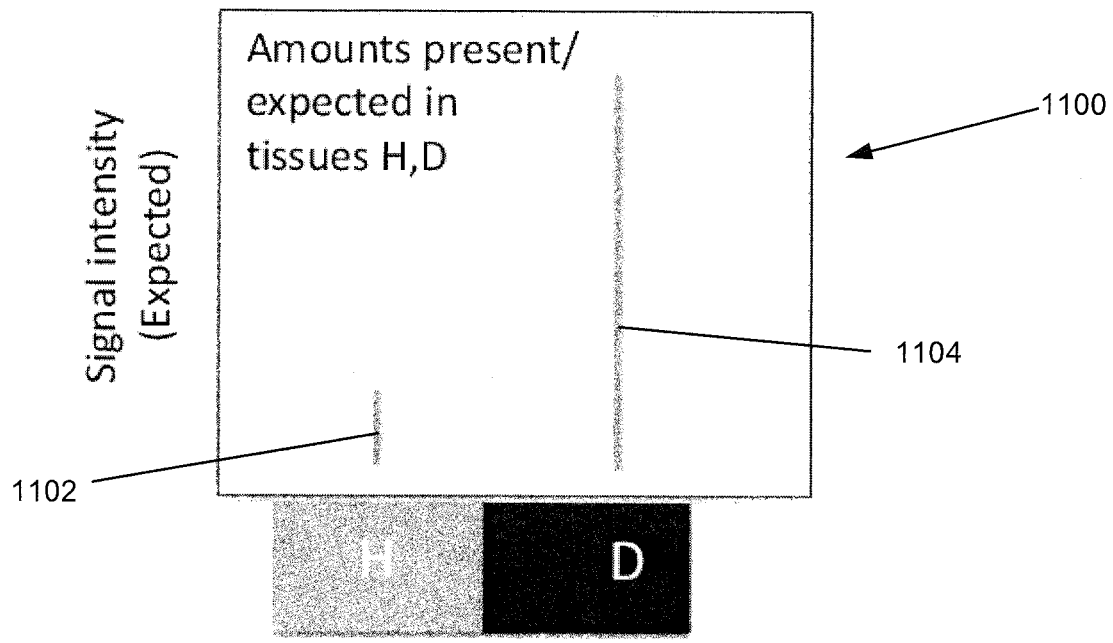
FIG. 11A is a diagram illustrating a plot of the expected abundance of an exogenous marker in three tissue regions.

Referring now to FIG. 11A, shown therein is a plot 1100 illustrating the abundance of an exogenous agent that would be expected in two tissue regions (H and D). The plot 1100 shows the expected signal intensity corresponding to a quantity of exogenous agent expected in each region.

In the example shown in FIG. 11A, tissue region H corresponds to a region of healthy tissue, whereas tissue region D corresponds to a region of diseased tissue. Accordingly, the exogenous agent is expected to be more abundant in the region of diseased tissue. Thus, detection of a region having a greater abundance of exogenous agent may indicate a region of interest. Thus, as shown in FIG. 11A, an expected healthy region abundance 1102 is much lower than the expected disease region abundance 1104.

Figure 11B:
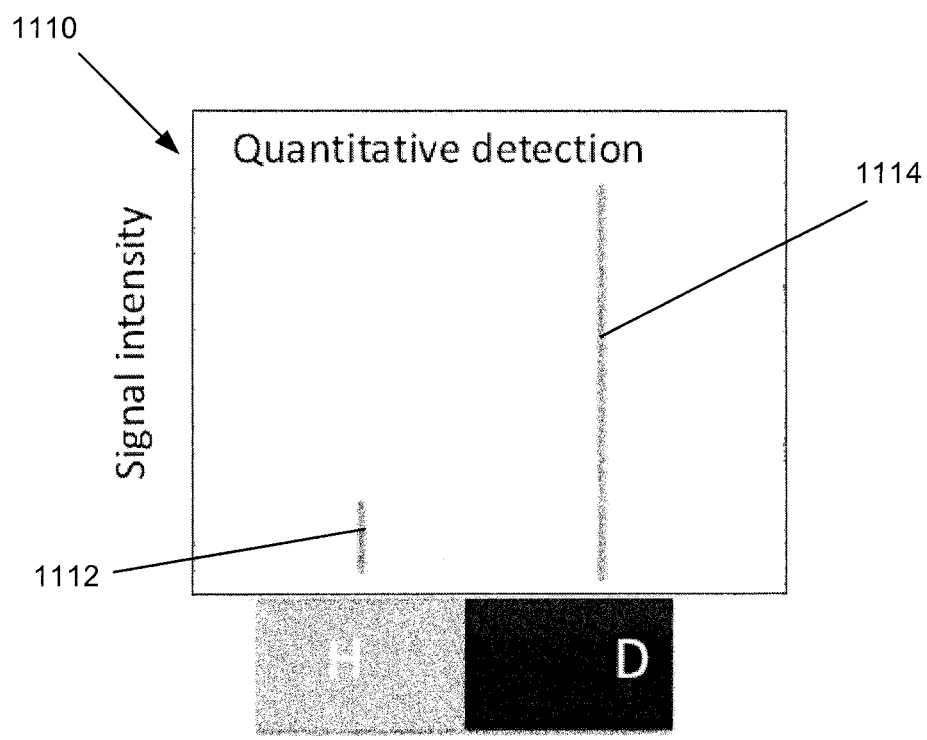
FIG. 11B is a diagram illustrating a plot of the measured abundance of an exogenous marker in three tissue regions using quantitative MS.

As can be seen from FIG. 11B, the first region abundance 1102, second region abundance 1104 and third region abundance 1106 are almost identical to the expected abundances shown in FIG. 11A.

Referring now to FIG. 11B, shown therein is a plot 1110 illustrating the detected abundance of the exogenous agent administered in the tissue regions H and D of FIG. 11A measured using a quantitative mass spectrometry method, such as quantitative ICP-MS. As can be seen from FIG. 11B, the detected healthy region abundance 1112, and the detected disease region abundance 1114 correspond to the expected abundances shown in FIG. 11A.

Figure 11C:
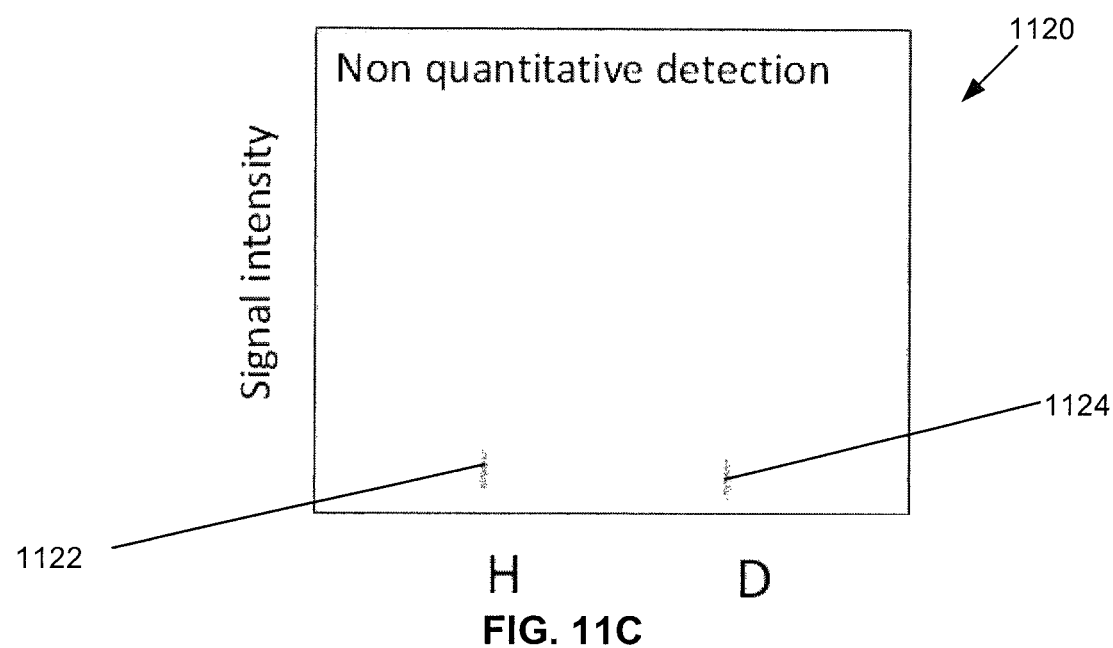
FIG. 11C is a diagram illustrating a plot of the measured abundance of an exogenous marker in three tissue regions using qualitative MS.

Referring now to FIG. 11C, shown therein is a plot 1120 illustrating the detected abundance of the exogenous agent administered in the tissue regions H and D of FIG. 11A measured using a qualitative analysis method. As can be seen from FIG. 11C, although the detected healthy region abundance 1122 corresponds well to the expected abundance for the healthy region 1102, the detected diseased region abundance 1124 does not correspond to the expected abundance for the disease region 1104. Furthermore, the detected diseased region abundance 1124 is similar to the detected healthy region abundance 1122. This may cause inaccurate identification of the boundary between the disease and healthy regions.

In some cases, exogenous agents will not possess 100% specificity for a region of interest that is desired to be identified or mapped. Accordingly, in such cases there will be some quantity of the exogenous agent present in the tissues surrounding the region of interest. For example, where the region of interest is a tumor, then in these cases some quantity of exogenous agent may also be present in healthy tissue surrounding the tumor. In such cases, a method of detecting the exogenous agent that is not quantitative may not provide as reliable mapping of the region of interest and the boundary of the region of interest.

For example, a detection method that only provides binary presence/absence information about the distribution of an exogenous agent (such as the example shown in FIG. 11C), may not provide as accurate an assessment of the region of interest. Accordingly, a quantitative, matrix-independent method, such as those described herein (e.g. embodiments employing ICP-MS) may provide more robust assessment of tumor boundaries. Nonetheless, qualitative detection of the distribution of an administered exogenous agent may still provide an indication of regions of interest, albeit with potentially less specificity.

Experimental Results

Figure 3A:
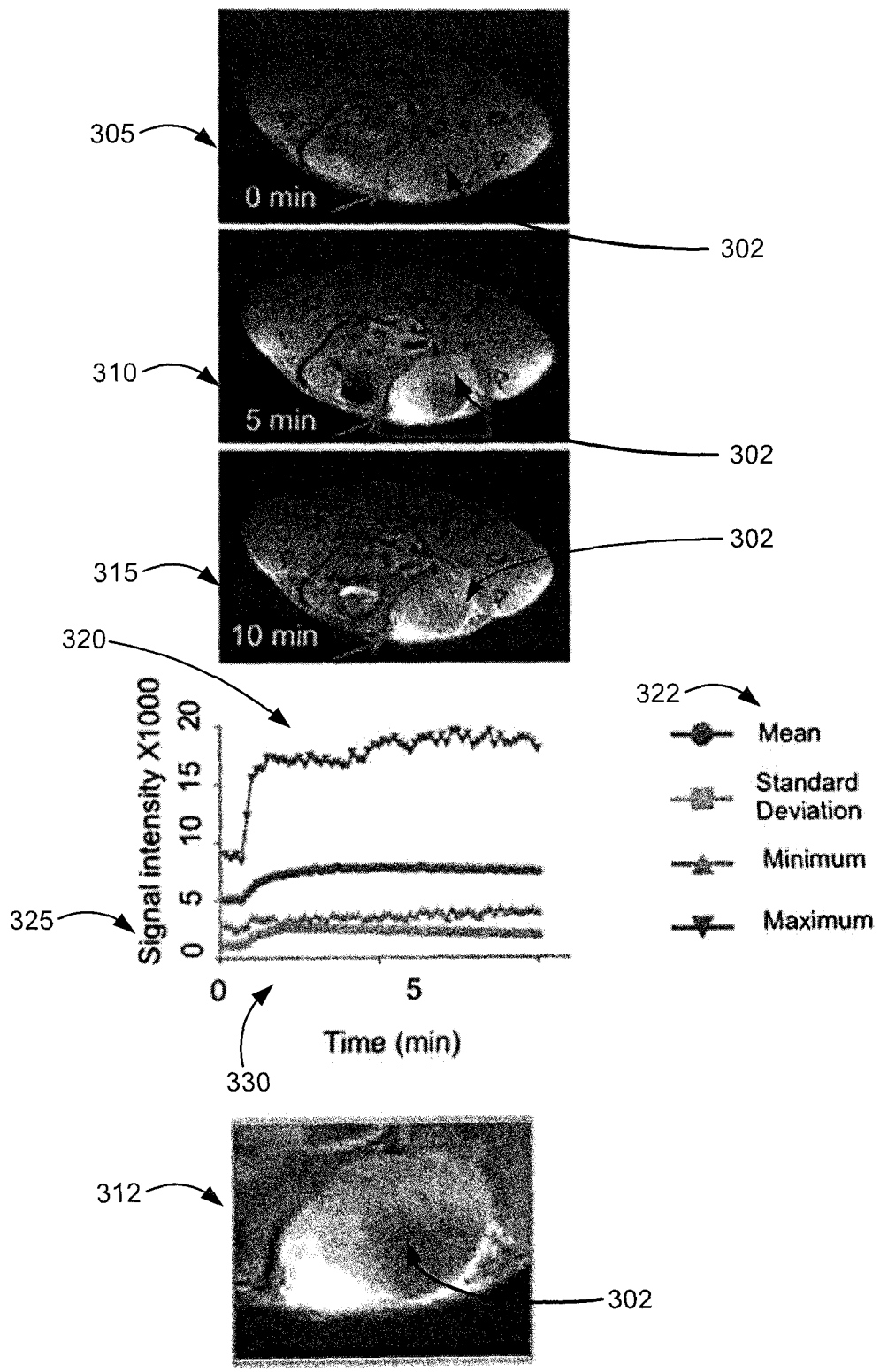
FIG. 3A is a diagram illustrating the results of magnetic resonance imaging of an exogenous agent passively targeted to breast cancer tumors in live mice.
Figure 3B:
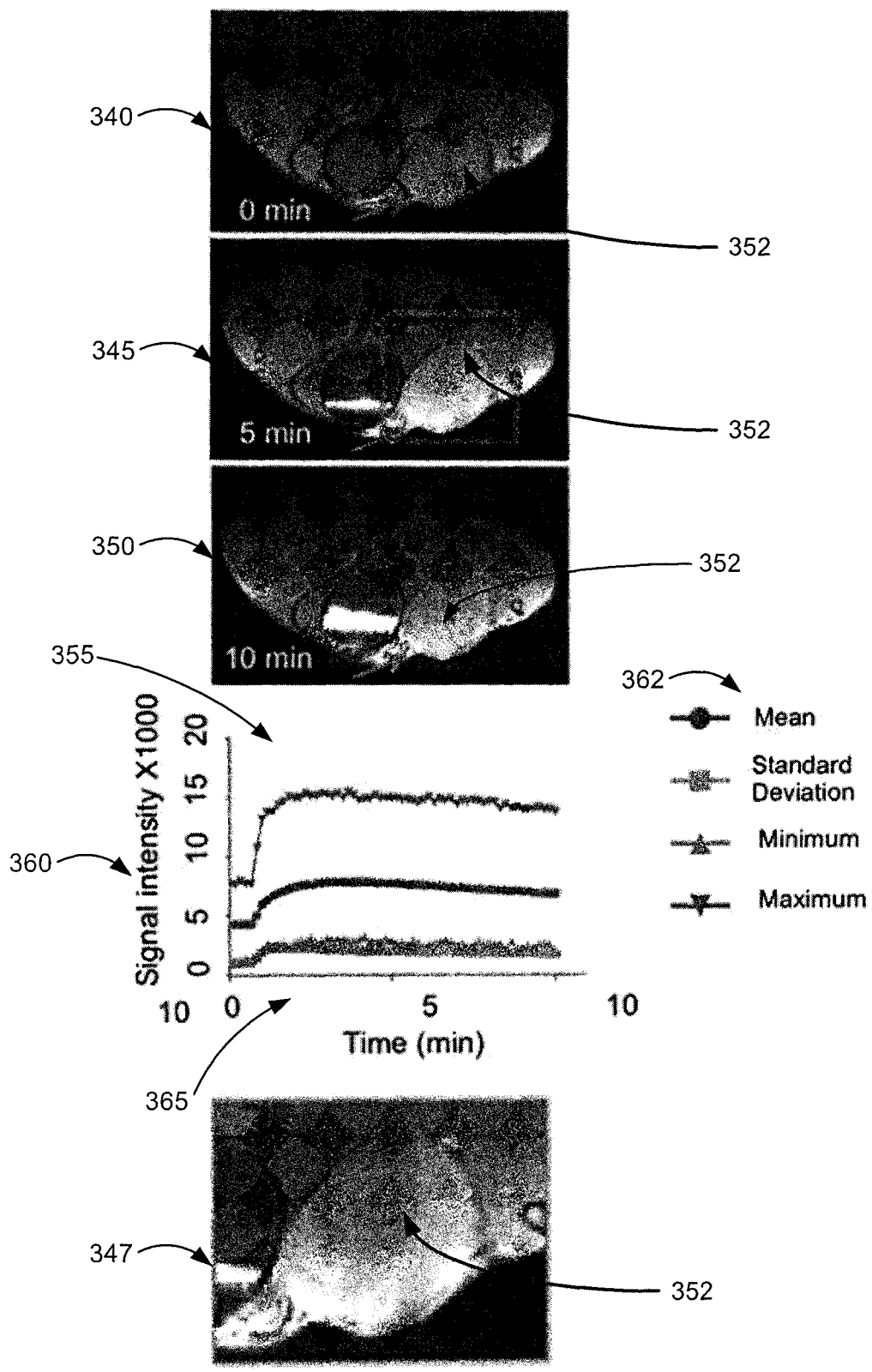
FIG. 3B is another diagram illustrating the results of magnetic resonance imaging of an exogenous agent passively targeted to breast cancer tumors in live mice.

Referring now to FIGS. 3A and 3B, shown therein are the results of kinetic DCE magnetic resonance imaging of an exogenous contrast agent (in this example Gadoteridol) that was passively targeted to breast cancer tumors in live mice. In both cases, Gadoteridol was intravenously injected into the tail vein of mice under anesthesia with isofluorane.

A first MR image 305 was taken at the time of injection. The tumor site 302 does not yet show the contrast agent in the first MR image 305. A second MR image 310 was taken at 5 minutes post injection. In the second MR image 310, the tumor site 302 exhibits maximal contrast enhancement. A zoomed image 312 shows the contrast enhancement of the tumor site 302 after being administered with the exogenous agent.

Plot 320 shows the change in the signal intensity 325 seen from the tumor site 302 over time 330 following injection. As indicated by legend 322, the maximum signal intensity appears to reach its peak in plot 320 after 5 minutes. The exogenous agent was seen to penetrate and diffuse into the tumor core from the peripheries of the tumor. A third MR image 315 taken at 10 minutes post injection shows similar contrast enhancement of the tumor site 302 as the second MR image 310.

Referring now to FIG. 3B, here again a first MR image 340 was taken at the time of injection and the tumor site 352 does not yet show enhancement by the contrast agent. A second MR image 345 was taken at 5 minutes post injection. In the second MR image 345, the tumor site 352 exhibited maximal contrast enhancement as shown in plot 355.

Plot 355 shows the change in signal intensity 360 over time 365 of the MR images taken of the breast cancer tumors. As can be seen from plot 355 and the corresponding legend 362, the signal intensity reaches its peak just before 5 minutes post-injection with the exogenous agent.

A zoomed image 347 shows the contrast enhancement of the tumor site 352 at 5 minutes after injection with the Gadoteridol. A third MR image 350 taken at 10 minutes post injection shows similar contrast enhancement of the tumor site 352 as the second MR image 345.

To obtain the mass spectrum plots shown in FIG. 4 below, a stock solution of the contrast agent ProHance® (Gadoteridol, 279.3 mg/mL) from Bracco Imaging containing 500 mM Gadoteridol was used to optimize the spray solvent, and to tune the instrument parameters. A volume of 1 μL was spotted on a glass slide, allowed to dry out for 10 minutes, and then analyzed by DESI-MS and DESI-MS/MS.

All the DESI-MS experiments described herein were performed using a Thermo Fisher Scientific LTQ mass spectrometer (San Jose, Calif., USA). Data was acquired and processed using QualBrowser Xcalibur 2.0 (Thermo Fisher Scientific). Mass spectra were acquired as full scans, in the positive ion mode, over the mass to charge ratio range from m/z 500 to 900. Typical instrumental parameters used were 4.5 kV capillary voltage and 275° C. capillary temperature. An $H_2O$-MeOH (1:1) solution was used as the spray solvent and delivered at the flow rate of 1.5 μL min-1. Methanol (MeOH) and ultra-pure water ($H_2O$), both HPLC-MS grade, were purchased from Sigma Aldrich (Oakville, ON, Canada). The sprayer-to-surface distance was 1.0 mm, the sprayer to inlet distance was 6-8 mm, an incident spray was set at 54°, and a collection angle of 10° was used. Tandem mass spectrometry (MS/MS), using collision-induced dissociation with collision energy of 15-25% (manufacturer's unit) was performed to confirm contrast agent in the tissues, and compared to MS/MS characterization of the Gadoteridol standard in Prohance®. Depending on various factors such as the type of mass spectrometer used, the analysis interface used, the tissue type being sampled and the exogenous agent being used, the specific analysis parameters described above may be adjusted to optimize the analysis, as will be appreciated by one skilled in the art.

In order to acquire DESI-MS images from the control tissue sample and contrast agent containing tissue samples discussed below with reference to FIGS. 5A and 6A, the tissues were scanned using a 2D moving stage in horizontal rows separated by 150 μm vertical steps until the entire sample was imaged. The lines were scanned at a constant velocity in the range of about 248 to 414 m/s and the scan time was set in the range of about 0.43 to 0.56 S. A lateral spatial resolution (pixel size) in the range of about 150 μm may be achieved under these conditions.

The MS spectra were processed using QualBrowser Xcalibur 2.0. The software platform ImageCreator version 3.0 was used to convert the Xcalibur 2.0 mass spectra files (.raw) into a format compatible with BioMap (freeware, http://www.maldi-msi.org/), which was used to process the mass spectral data and to generate 2D spatially resolved ion images. Tentative assignments of lipids seen in the positive ion mode in kidney and tumor samples were made by comparing with published ESI results, which are shown in Table 1.

Figure 4:
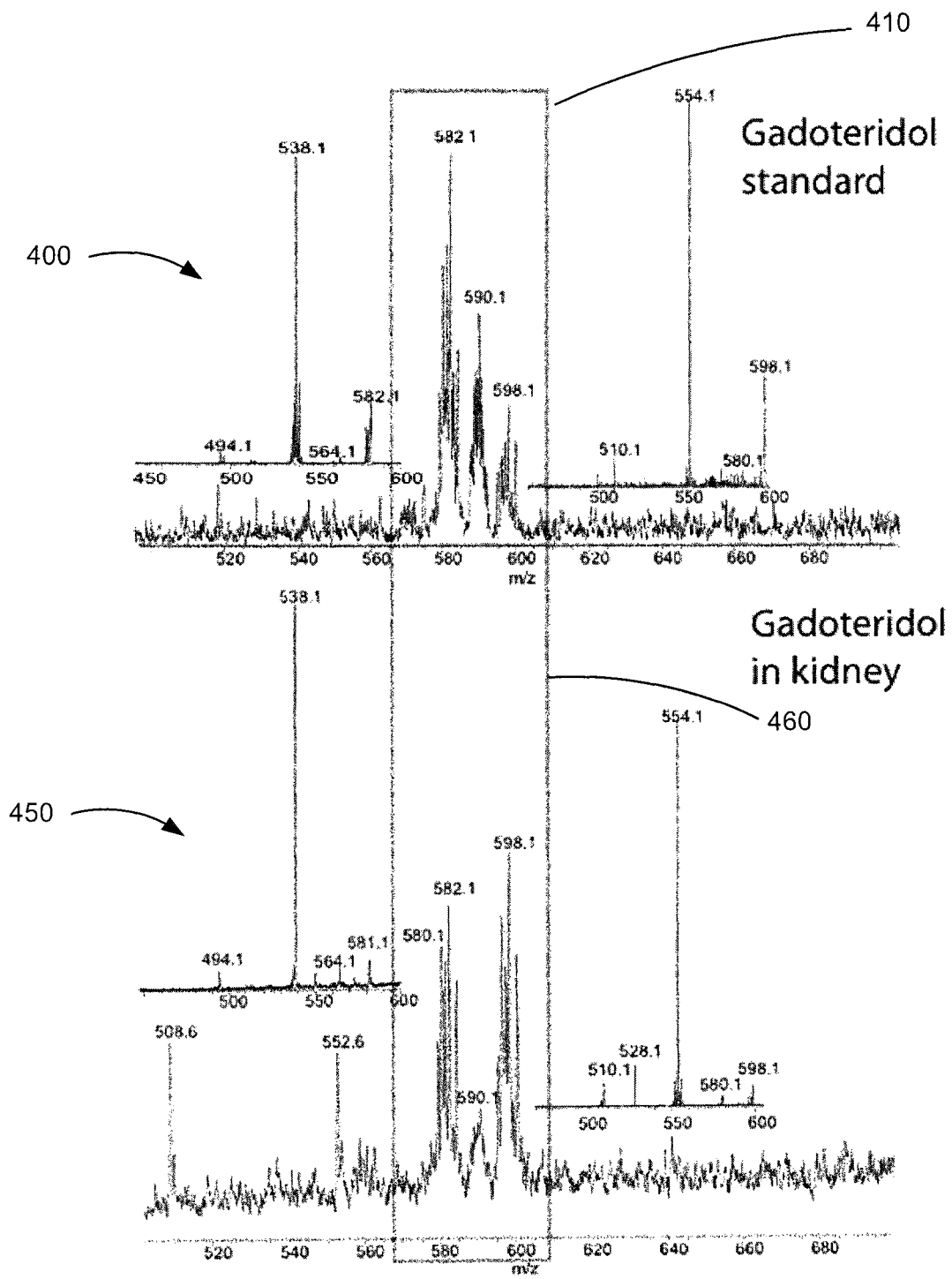
FIG. 4 is a diagram illustrating a plot of the mass spectrum of an exogenous agent absorbed on the surface of a glass slide and inside mouse kidneys using DESI-MS.

Referring now to FIG. 4, shown therein is a first plot 400 of the mass spectrum of an exogenous agent, in this case Gadoteridol, absorbed on a glass slide. FIG. 4 also shows a second plot 450 of the mass spectrum of Gadoteridol inside mouse kidneys at 5 minutes post intravenous injection. The mass spectrum plots 400 and 450 were obtained using DESI-MS imaging. The MS/MS fragmentation pattern of the major Gadoteridol adducts ([Gadoteridol+Na]+ (m/z 582.1) and [Gadoteridol+K]+ (m/z 598.1)) can be seen in both plots 400 and 450 as well as the resulting characteristic losses of water (564.1 m/z), $CO_2$ (m/z 538.1) and $2CO_2$ (m/z 494.1) molecules.

The insets 410 and 460 highlight the mass-to-charge signal of Gadoteridol in the mass spectrum from the surface of the glass slide and the mouse kidneys respectively. In the kidney inset 460, the ratio between [Gadoteridol+Na]+ and [Gadoteridol+K]+ is different from the ratio seen in inset 410 of the standard compound under identical spray, collection and instrument tuning conditions. However, consistent fragmentation patterns in the ex vivo tissue-borne Gadoteridol (plot 450) and the standard compound in vitro (plot 400) corroborate the presence of Gadoteridol inside mouse kidneys at 5 minutes post intravenous injection.

Referring now to Table 1, shown therein is a representative mass spectrum of endogenous lipid signatures characteristic to mouse kidneys and breast cancer tumors. The m/z values are derived from previous studies published in the literature (see for example, Milne, S. et al. *Methods* 2006, 39, 92; Janfelt, C. et al. *Journal of mass spectrometry: JMS* 2013, 48, 361). These signatures represent tentative assignment of lipids seen in the positive ion mode images of mouse kidneys and breast cancer tumors.

To obtain the images shown below in FIGS. 5A-5C and FIGS. 6A-6C, SCID mice (from Harlan Laboratories) were inoculated in the lower mammary fat pad with 3×106 human MDA-MB-231 triple negative metastatic breast cancer cells and housed for 3 weeks to grow tumors up to 1 cm in diameter (caliper measurements). ProHance® was administered intravenously into the tail vein of the tumor bearing SCID mice using a 29 to 31 gauge needle attached to either a syringe or a catheter. Up to 100 µL/25 g of body weight of Prohance® was administered to each animal. MR imaging was conducted at the University Health Network's (UHN) Spatio-Temporal Targeting and Amplification of Radiation Response Program (STTARR), and animals were induced using a 5% of isofluorane/oxygen or air mixture and then transferred onto the imaging stage using a 2% isofluorane/oxygen or air mixture. Throughout the imaging sessions, the animals' breathing was monitored using a respiratory pad and a respiratory tracking system (when imaged on the 1T Aspect or 7T Bruker MRI system, ~30 min per imaging session).

After a complete washout of the Gadoteridol signal took place (as verified by MR imaging), the mice were injected again with a second dose of Gadoteridol as described above, sacrificed with an overdose of isofluorane and subjected to the surgical removal of kidneys and tumors. Extracted tissues were subsequently frozen using liquid $N_2$ vapor and stored at −80° C. until they were sectioned using a cryotome (a CM 1950 from Leica Biosystems with a thickness of 20 µm. The tissue sections were thaw mounted onto glass slides. The glass slides containing two 20 µm consecutive slices were mounted on a lab-built 2D moving stage using tape and subjected to 2 dimensional DESI-MS and DESI-MS/MS analysis. The MS parameters were tuned, and MS/MS verification of the contrast agent was obtained using the first slice and DESI imaging was performed using the second tissue slice present on the same glass slide without altering the collection geometry. For each tissue slice subjected to DESI imaging, a consecutive 5 µm thin slice was taken for standard staining and pathology assessments.

TABLE 1

| m/z | Tentative assignment from literature |
| --- | --- |
| 703.5 | [SM 16:0 + H]+ |
| 725.5 | [SM 16:0 + Na]+ |
| 741.5 | [SM 16:0 + K]+ |
| 746.5 | [PCp (34:0) + H]+ a/o [PCe (34:1) + H]+ |
| 756.6 | [PC (32:0) + Na]+ |
| 772.3 | [PC (32:0) + K]+ |
| 780.6 | [PC (36:5) + H]+ and[PC (34:2) + Na]+ |
| 782.6 | [PC (36:4) + H]+ and/or [PC (34:1) + Na]+ |
| 798.5 | [PC (34:1) + K]+ |
| 802.6 | [PC (36:5) + Na]+ |
| 804.6 | [PC (38:7) + H]+ a/o[PC (36:4) + Na]+ |
| 820.6 | [PCp (40:5) + H]+ a/o [PCe (40:6) + H]+ |
| 824.6 | [PCp (40:3) + H]+ a/o [PCe (40:4) + H]+ |
| 828.6 | [PCp (40:1) a/oPCe (40:2) + H]+ a/o[PC (38:6) + Na]+ |
| 814.6 | [PCp (38:5) a/oPCe (38:6) + H]+ a/o [PC (38:2) + Na]+ |
| 830.6 | [PC(38:5) + Na]+ |
| 832.6 | [PC (38:4) + Na]+ |
| 844.5 | [PC (38:6) + K]+ |
| 846.6 | [PC (40:0) + H]+ |
| 856.6 | [PC (40:6) + Na]+ |
| 872.6 | [PC (40:6) + K]+ |

Figure 5A:
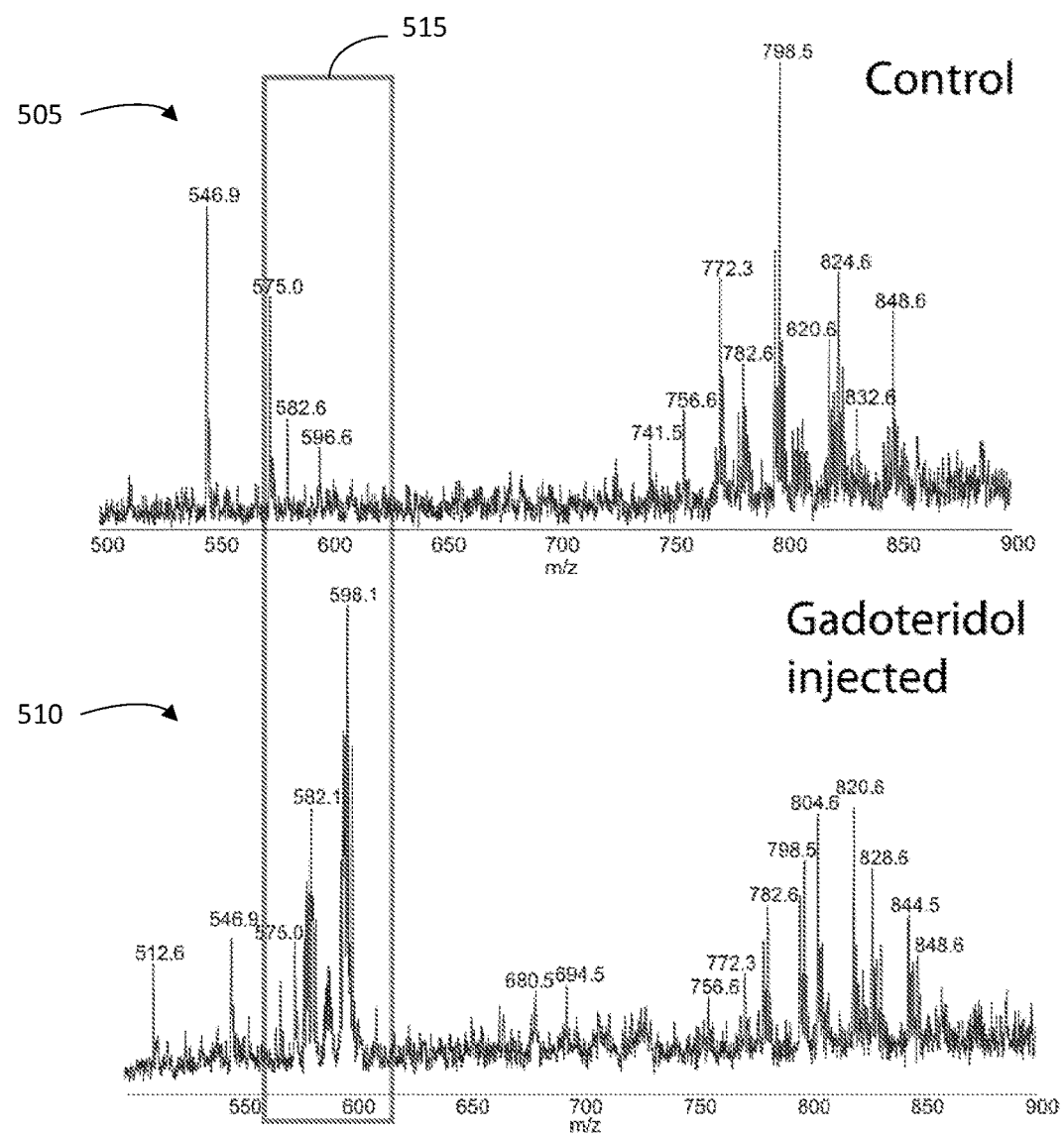
FIG. 5A is a diagram illustrating a plot of the mass spectrum of a breast cancer tumor from a mouse and the mass spectrum of the breast cancer tumor after administration of an exogenous agent to the mouse.

Referring now to FIG. 5A, shown therein is a first plot 505 illustrating the mass spectra of control human breast cancer tumors in a mouse contrasted with a second plot 510 illustrating the mass spectra of human breast cancer tumors in a mouse labelled using an exogenous agent, which in this case is Gadoteridol. The mouse was intravenously injected with the contrast agent and sacrificed at 5 minutes post injection.

The mass spectrum plots 505 and 510 were obtained by performing DESI-MS on the samples from the control breast cancer tumor and the labelled breast cancer tumor. The inset 515 shows the distribution pattern of the major species populating the m/z profile of Gadoteridol, [Gadoteridol+K]+ of m/z 598.1, [Gadoteridol+Na]+ of m/z 582.1 as well as [2Gadoteridol+Na+K]++ of m/z 590.1. Similar to the kidney results shown in FIG. 6 below, m/z signals characteristic to both Gadoteridol as well as some endogenous tumor lipids from Table 1 were observed.

Figure 5B:
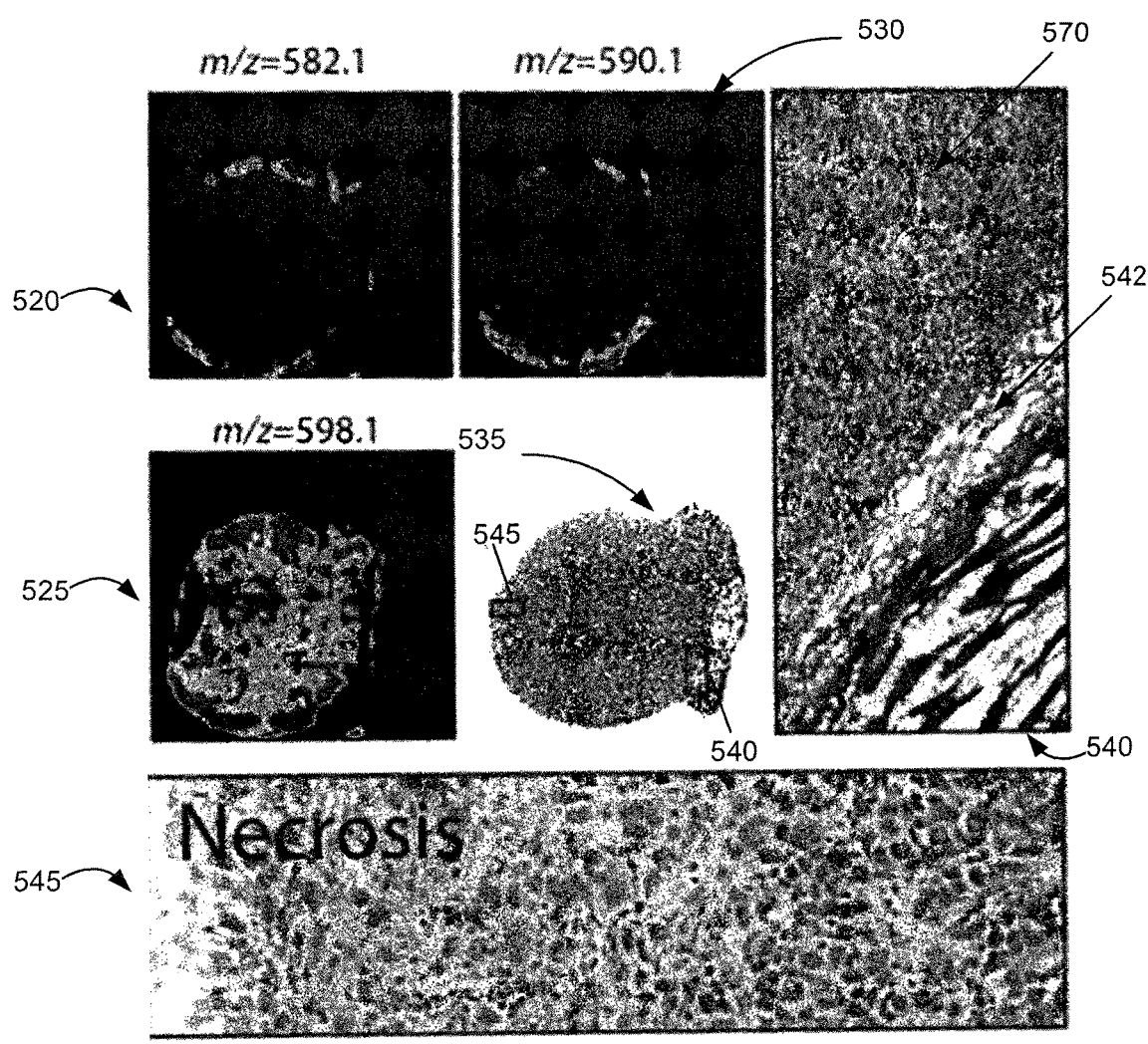
FIG. 5B is a diagram illustrating the spatial distribution pattern of various elements of the exogenous agent inside the breast cancer tumor whose mass spectrum is shown in FIG. 5A.

Referring now to FIG. 5B, shown therein are images of slices of the breast cancer tumor excised from the mouse that were labelled using the exogenous agent Gadoteridol. MS images 520, 525, and 530 illustrate the spatial distribution of the major species of Gadoteridol within the breast cancer tumor. The MS images 520, 525, and 530 were obtained using two-dimensional DESI-MS imaging with 150 um resolution at different m/z ratios.

An H&E stained image 535 of the tumor is also shown. Zoomed inset 540 shows the boundary 542 between the tumor 570 and the adjacent muscle tissue. Zoomed inset 545 shows evidence of necrosis in a region of the tumor located distally from the muscle tissue.

Similar to FIG. 3, the exogenous agent in MS images 520, 525, and 530 has the highest signal at the outer edge of the tumor. Accordingly, the exogenous agent appears to penetrate the tumor structure from the periphery. In MS image 525, [Gadoteridol+K]+ of m/z 598.1 was seen throughout the tumor except in regions revealed by H&E to be necrotic (see zoomed image 545), while the [Gadoteridol+Na]+ of m/z 582.1 and [2Gadoteridol+Na+K]++ of m/z 590.1 adducts were seen at the periphery of the tumor at 5 minutes post injection (MS images 520 and 530 respectively).

Comparing the MS images 520, 525, and 530 to the H&E stained images 535, 540, and 545 the necrotic region of the breast cancer tumor is seen to possess no Gadoteridol signal. This observation is corroborated by the knowledge that contrast enhancement of necrotic tumors by Gadolinium-based contrast agents is only possible after special parameterization of the MR signal. The lack of contrast enhancement in the necrotic regions may be due to the absence of the contrast agent in these regions, as opposed to aberrant mechanisms affecting relaxation modulation during contrast enhancement in MR imaging. As such, the use of mass spectrometry to probe the localization of contrast agents within biological tissues may shed further light on how to optimally utilize passive targeting of exogenous agents for medical imaging. This mode for targeting exogenous agents to tumor sites is widely used for signal enhancement in many other ubiquitously used clinical imaging modalities.

Figure 5C:
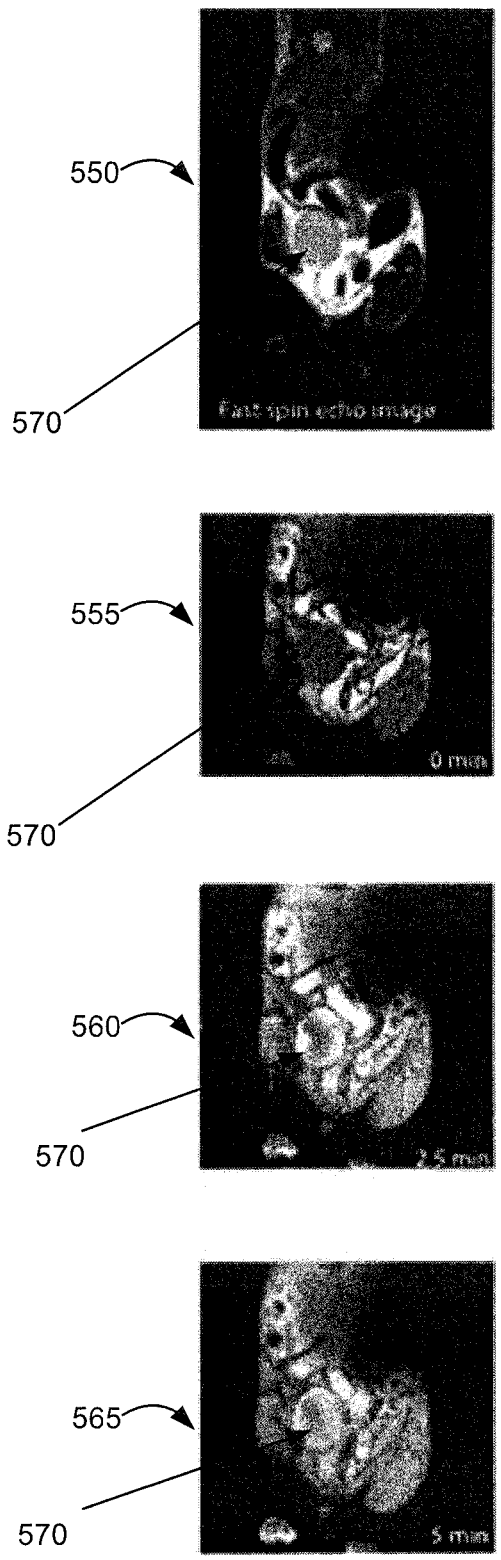
FIG. 5C is a diagram illustrating magnetic resonance images of the breast cancer tumor in a live mouse prior to administration of an exogenous agent and at time delays after administration of the exogenous agent.

Referring now to FIG. 5C, shown therein are MR images of contrast enhancement in a live mouse showing the flux of the exogenous agent through the breast cancer tumor that was subsequently extracted and subject to DESI-MS, the results of which are shown in FIGS. 5A and 5B. A fast spin echo image 550 of the mouse prior to injection with the exogenous agent illustrates the mouse anatomy. Subsequent MR images 555, 560, and 565 were taken at the time of injection, 2.5 minutes post-injection and 5 minutes post-injection respectively. Tumor 570 indicates the breast cancer tumors that were harvested and shown in FIG. 5B.

Figure 6A:
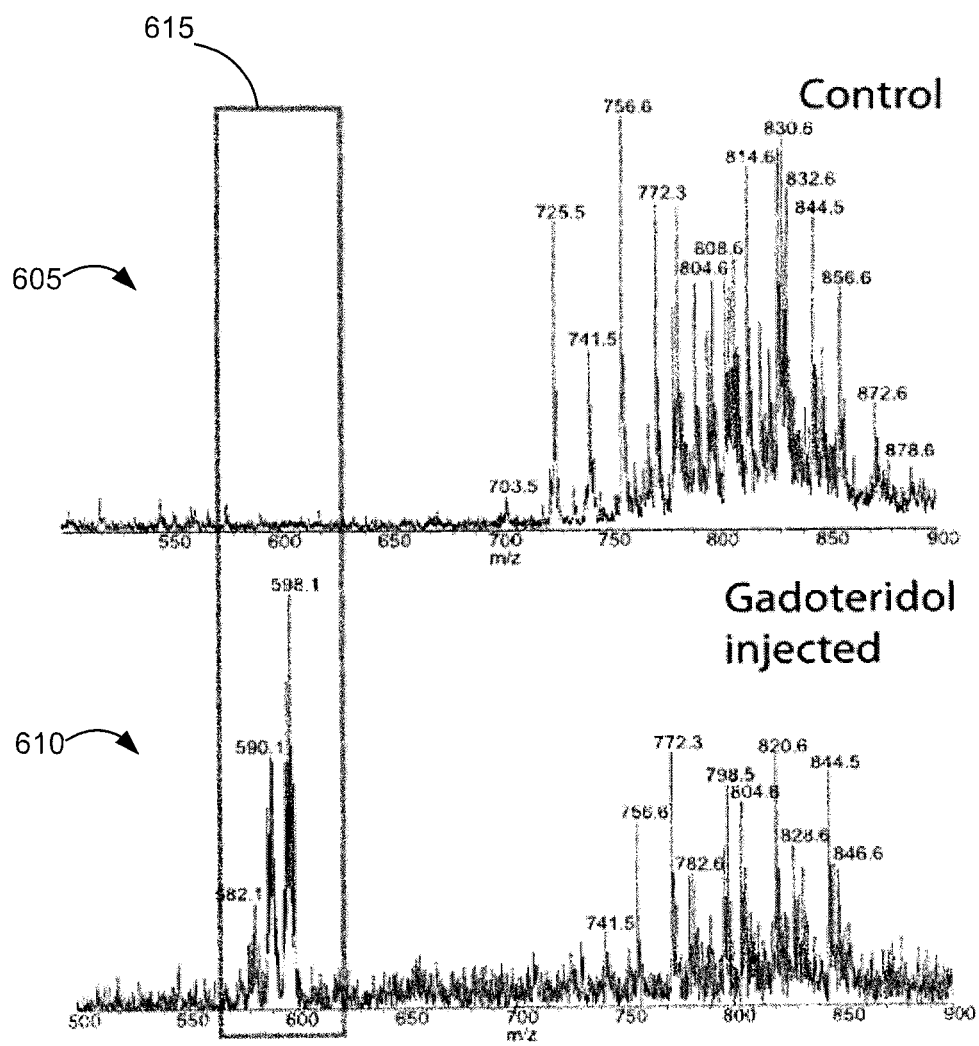
FIG. 6A is a diagram illustrating a plot of the mass spectrum of the kidneys of a mouse and the mass spectrum of the kidneys after administering an exogenous agent to the mouse.

Referring now to FIG. 6A, shown therein is a first plot 605 illustrating the mass spectra of control mouse kidneys contrasted with a second plot 610 illustrating the mass spectra of mouse kidney labelled using Gadoteridol. The mouse was intravenously injected with the contrast agent and sacrificed at 5 minutes post injection.

The mass spectrum plots 605 and 610 were obtained by performing DESI-MS imaging of mouse kidneys with 150 um resolution. The mass spectrum plot 610 of the mouse kidney injected with Gadoteridol shows both the endogenous lipid signatures characteristic to the kidney (see Table 1) as well as m/z peaks typical to Gadoteridol, as discussed above with reference to FIG. 4.

The inset 615 highlights the distribution pattern of the major species populating the m/z profile of Gadoteridol, [Gadoteridol+K]+ of m/z 598.1, [Gadoteridol+Na]+ of m/z 582.1 and [2Gadoteridol+Na+K]++ of m/z 590.1. These distribution patterns were corroborated with H&E images of the consecutive slice shown in FIG. 6B.

Figure 6B:
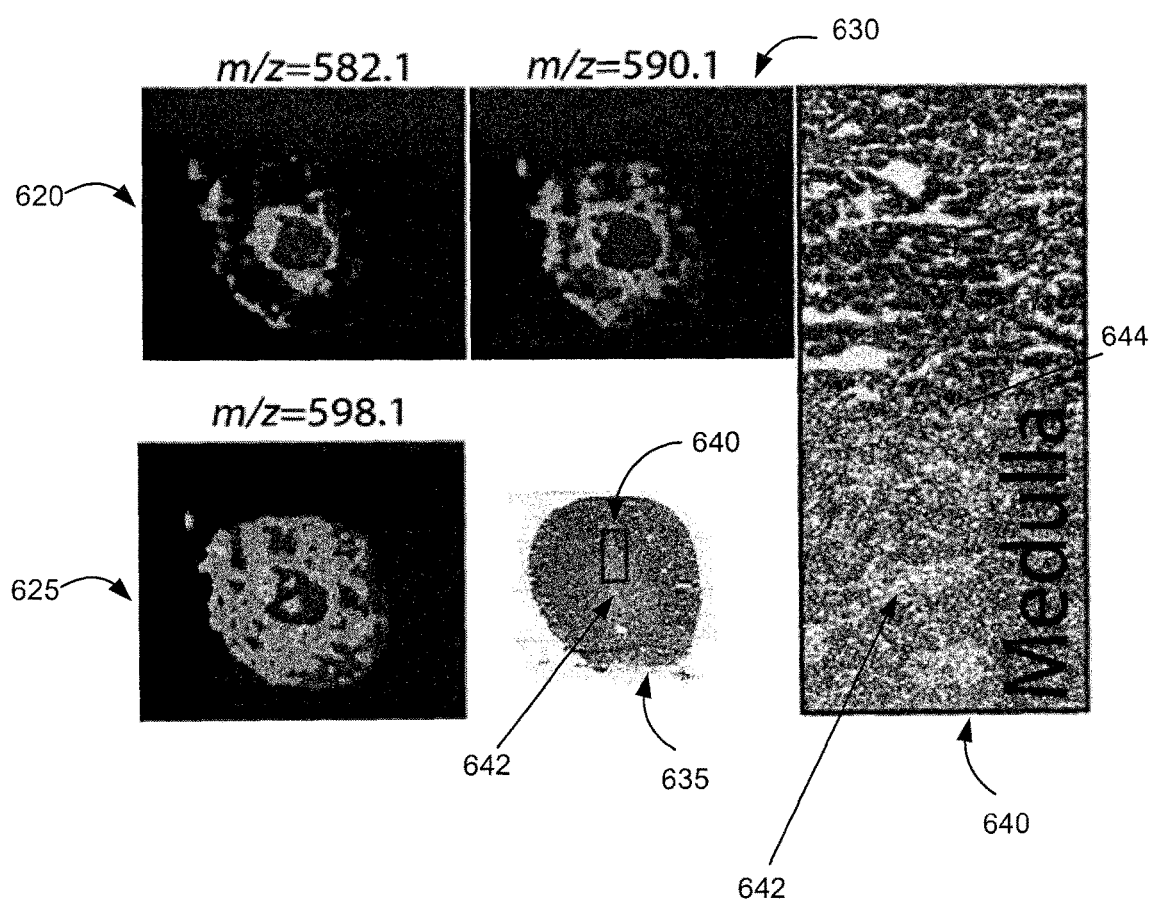
FIG. 6B is a diagram illustrating the spatial distribution pattern of the exogenous agent within the mouse kidney of FIG. 6A.

Referring now to FIG. 6B, shown therein are images of slices of a mouse kidney labelled using Gadoteridol. MS images 620, 625 and 630 illustrate the spatial distribution of Gadoteridol within the mouse kidney. MS images 620, 625 and 630 were obtained using two-dimensional DESI-MS imaging with 150 µm resolution and are shown for different m/z ratios.

The slice 635 of the mouse kidney immediately consecutive to the slice that was mass spectrometry image was H&E stained. In the kidney, [Gadoteridol+Na]+ of m/z 582.1, [Gadoteridol+K]+ of m/z 598.1 and [2Gadoteridol+Na+K]++ of m/z 590.1 all localize to the medulla region 642 as evident from the H&E staining. The zoomed in view 640 of the boundary 644 of the region with maximal Gadoteridol m/z localization on the H&E indicates localization of the agent to the medulla region 642 of the kidney.

Figure 6C:
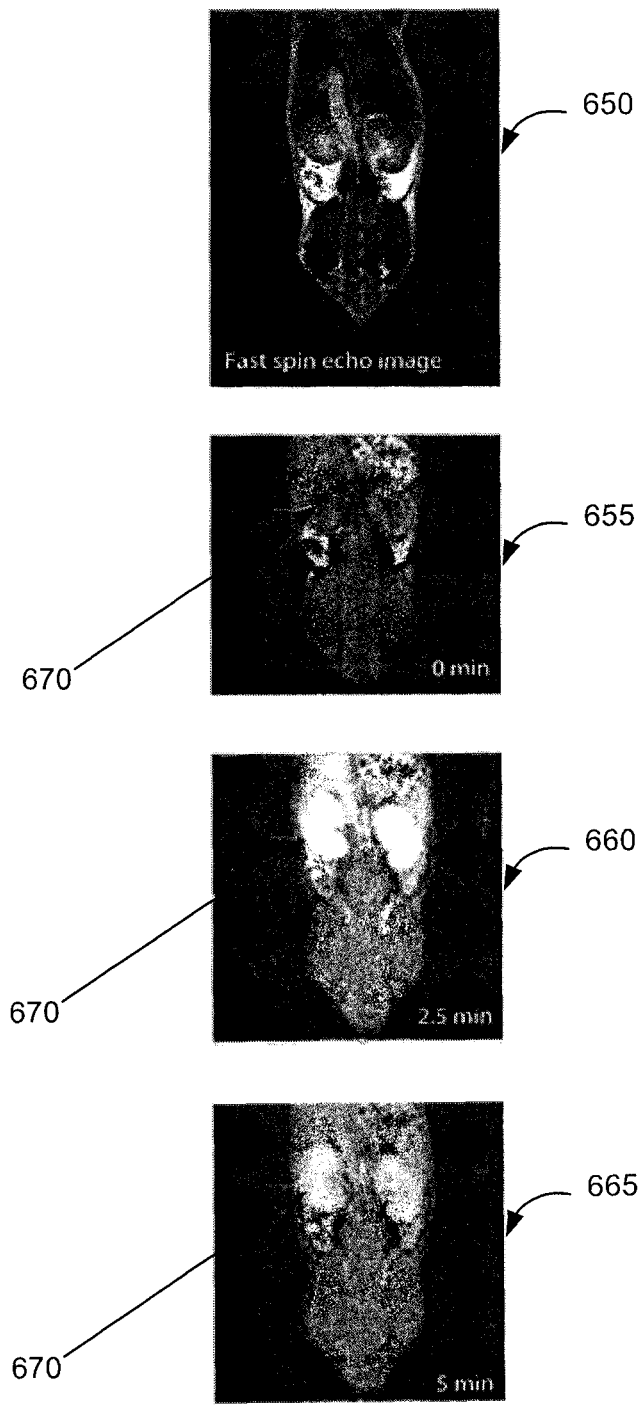
FIG. 6C is a diagram illustrating magnetic resonance images of kidneys of a live mouse prior to administration of an exogenous agent and at time delays after administration.

Referring now to FIG. 6C, shown therein are Dynamic Contrast Enhanced (DCE) MR images of contrast enhancement in a live mouse showing the flux of Gadoteridol through the same kidney that was subsequently extracted and subjected to DESI mass spectrometry post injection in FIGS. 6A and 6B. A fast spin echo image 650 of the mouse prior to intravenous injection with Gadoteridol is shown to illustrate the mouse anatomy. Subsequent MR images 655, 660 and 665 were taken at the time of injection, 2.5 minute post-injection and 5 minutes post-injection respectively. The image 670 is of a slice of the kidneys before they were harvested and FIG. 6B shows a slice of the harvested kidneys for different m/z ratios.

After a complete washout of the Gadoteridol signal from the primary injection delivered for the purpose of kinetic MR imaging took place, a secondary intravenous injection into the tail vein was performed, and the kidneys were harvested at 5 minutes post injection for mass spectrometry imaging.

Referring now to FIG. 9A, shown therein is an image 900 of pancytokeratin (PCK) immunocytochemistry staining of the epithelial cells of a mouse injected with a human breast cancer tumor cell line 902. The breast cancer tumor cell line 902 has a darker shade resulting from the PCK immunocytochemistry staining. The staining also reveals the boundary 905 of the tumor region.

Referring now to FIG. 9B, shown therein is an overlay image 920 of a DESI-MS molecular image of [Gadoteridol+K]+ (m/z 598.1) overlaid on the PCK immunostained image 900 of the breast cancer tumor 902 shown in FIG. 9A. As shown in FIG. 9B, the exogenous agent 910 localizes to the tumor region 902 of the epithelial cells.

Referring now to FIG. 9C, shown therein is an overlay image 940 of the DESI-MS molecular image of [Gadoteridol+K]+ (m/z 598.1) shown in FIG. 9B overlaid on an H&E stained slice of the epithelial cells. H&E staining is a principal stain (often referred to as the gold standard) used in histology to examine biopsies of suspected cancers. Overlay image 940 indicates that the exogenous agent 910 is excluded from the muscle tissue 915 at the boundary 905.

As the exogenous agent 910 is excluded from the muscle tissue 915 at the tumor boundary 905, and is localized well with areas of epithelial origin (via PCK immunohistochemistry) that are cancerous 902, this is indicative of the utility of exogenous agent mapping in both revealing regions of interest such as tumors and marking the boundary of the region of interest.

The localization of the exogenous agent ([Gadoteridol+Na]+ of m/z 582.1 in FIG. 9) to the tumor periphery, if shown to be a widespread signature of tumor vasculature, may be used (with intraoperative MS imaging systems such as those discussed herein) to map regions of tumor major vasculature that may be eliminated in a resection to cut out the blood supply to the rest of the tumor.

Referring to FIG. 10A, shown therein is an MS image 1000 showing the relative abundance of an exogenous agent in a breast cancer tumor. The MS image 1000 illustrates the ion abundances of Gadolinium (Gd) in breast cancer tumor determined using DESI-MS imaging.

Referring now to FIG. 10B, shown therein are the results of quantitative analysis of the distribution of an exogenous agent in a section of a breast cancer tumor. Here, ICP-MS was used to quantify the amount of Gadolinium (Gd) element in a 200 um thick section of the breast cancer tumor shown in FIG. 10A. The distribution of all three contributing Gadoteridol adducts (discussed above with reference to FIG. 4) are shown overlaid on an image of the tumor section.

To validate the ion abundances shown in the DESI-MS image 1000, a 200 µm think-slice of tumor was sectioned into three areas (1025, 1030 and 1040). The total tissue weight in each section was determined using an analytical balance and Gadoteridol was acid extracted for ICP-MS quantification. Gadoteridol was extracted using excess volume (e.g., 3.5 mls for every 1 mg tissue material in two rounds) of 10% perchloric acid through mixing and vortexing followed by a 30 min centrifugation at 21,000G taking the supernatant that was then diluted 5× with double distilled water. For ICP-MS analysis both the standard Gadoteridol solutions and the extracted samples were taken up in excess 2% nitric acid (1000 fold dilution) and were subjected to ICP-MS quantification using a Nexlon 350 ICP-MS (Perkin-Elmer).

The absolute values of the Gd elements determined in the ICP-MS quantification process (54 pg in the first area 1025, 12.8 pg in the second area 1030, and 27.5 pg in the third area 1040) shown in the ICP-MS image 1020 is in qualitative agreement with the combined ion abundances seen in the DESI-MS image 1000 from all contributing adducts. This observation further validates the relative abundance of the tumor-borne Gadoteridol signal seen in DESI-MS images of contrast-enhanced breast cancer tumor.

As shown in FIG. 10B, using exogenous agents with quantitative, matrix independent ICP-MS detection may offer a better and more robust assessment of tumor boundaries than previous imaging modalities. Furthermore, laser ablation mass spectrometry that offers fixed tissue volume desorption per pulse adds more precision to the quantitative picture offered by plasma ionization such as ICP ionization.

In some embodiments, laser desorption using nanosecond or picosecond infra-red sources, for example a picosecond infra-red laser (PIRL) may be combined with administration of exogenous agents to offer molecular guidance during surgery using ICP mass spectrometry of exogenous agents. Such embodiments may allow the transfer of gaseous particles to the mass analyzer to offer precise guidance for minimally invasive surgery with the absence of significant mechanical and thermal damage to tissues that surround the cut site.

Such embodiments may also provide an opportunity to miniaturize mass spectrometry devices that may be tuned to a selected range of m/z ratio for the metallic elements within the exogenous agents, which may be detected as a proxy for the contrast agent molecules that bear them. This may further facilitate adoption for more widespread intraoperative use where a mass analyzer having a compact footprint is a key attribute.

The sensitivity of mass spectrometry, in particular ICP-MS, allows for a much smaller amount of the exogenous agent to be used for imaging, resulting in potentially safer use of experimental, passively targeted agents that offer good disease site absorption yet are currently deemed too toxic to be used in clinical imaging using conventional modalities because they need to be used in higher amounts. This may also render the current practice of invasive intraoperative contrast enhanced imaging safer for all patients by enabling injection doses that are far below current requirements.

Figure 7B:
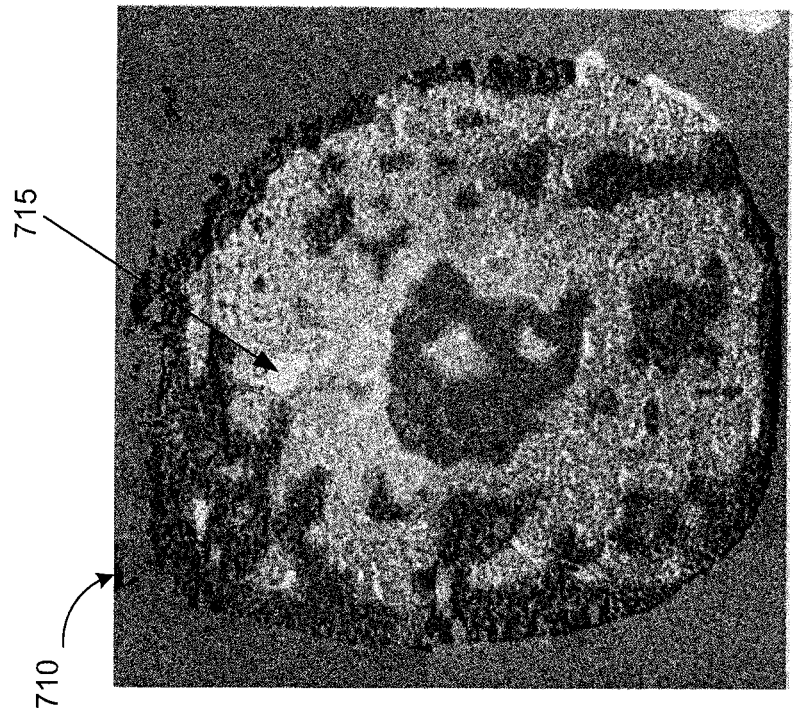
FIG. 7B is a diagram illustrating a localization pattern of an exogenous agent administered to the kidneys of the mouse of FIG. 7A.
Figure 7A:
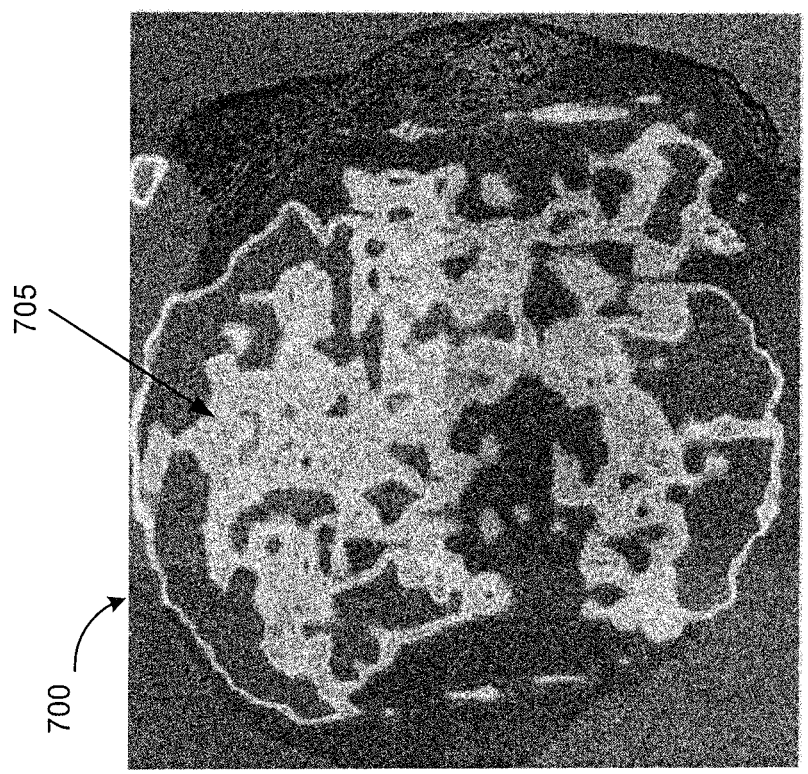
FIG. 7A is a diagram illustrating a localization pattern of an exogenous agent administered to a breast cancer tumor in a mouse.

Referring now to FIGS. 7A and 7B, shown therein are the results of DESI-MS imaging of the distribution of an example exogenous agent ([Gadoteridol+K]+ of m/z 598.1) in mouse tissues. The DESI-MS images shown in FIGS. 7A and 7B are shown overlaid on an H&E image of the tissue slice immediately consecutive to the tumor slice imaged with DESI MS.

FIG. 7A shows a molecular image 700 of the distribution 705 for a m/z of 598.1 in a breast cancer tumor determined using DESI-MS overlaid on an H&E image of the breast cancer tumor from the tissue slice consecutive to the slice imaged with DESI-MS. FIG. 7B shows a molecular image 710 of the distribution 715 for a m/z of 598.1 in a mouse kidney overlaid on an H&E image from the tissue slice consecutive to the mouse kidney slice imaged with DESI-MS. There is dissimilarity between the Gadoteridol localization pattern in the kidney MS image 710 and what is seen within the breast cancer tumor MS image 700.

In the breast cancer tumor MS image 700, the [Gadoteridol+K]+ of m/z 598.1 was seen throughout the tumor except in regions revealed by H&E to be necrotic. The [Gadoteridol+Na]+ of m/z 582.1 and [2Gadoteridol+Na+K]++ of m/z 590.1 adducts were seen at the periphery of the tumor MS image 700 at 5 minutes post injection.

Figure 8A:
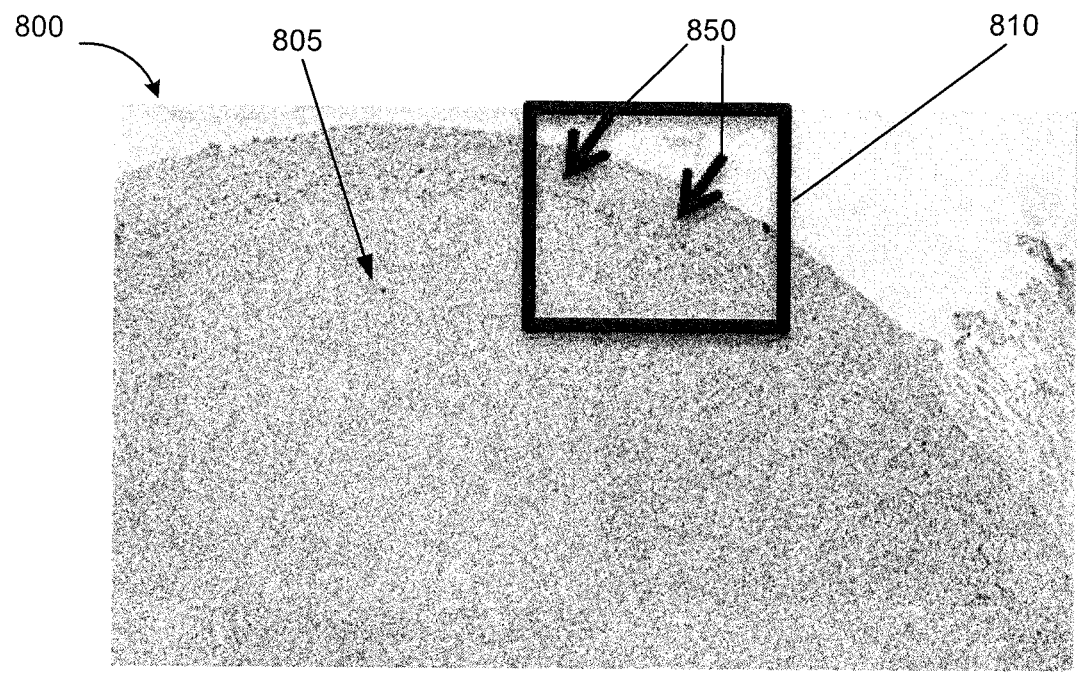
FIG. 8A is a diagram illustrating a CD31 immunostained image of a human breast cancer tumor excised from a mouse.

Referring now to FIG. 8A, shown therein is an image 800 of a breast cancer tumor 805 that has been immunostained using an anti-CD31 antibody. The CD31 immunostain reveals the location of blood vessels in the breast cancer tumor 805. The breast cancer tumor 805 corresponds to the breast cancer tumor shown in FIGS. 5A-C, discussed above. The immunostaining reveals that the regions 850 in the periphery of the tumor contain the majority of the tumor blood vessels.

Figure 8B:
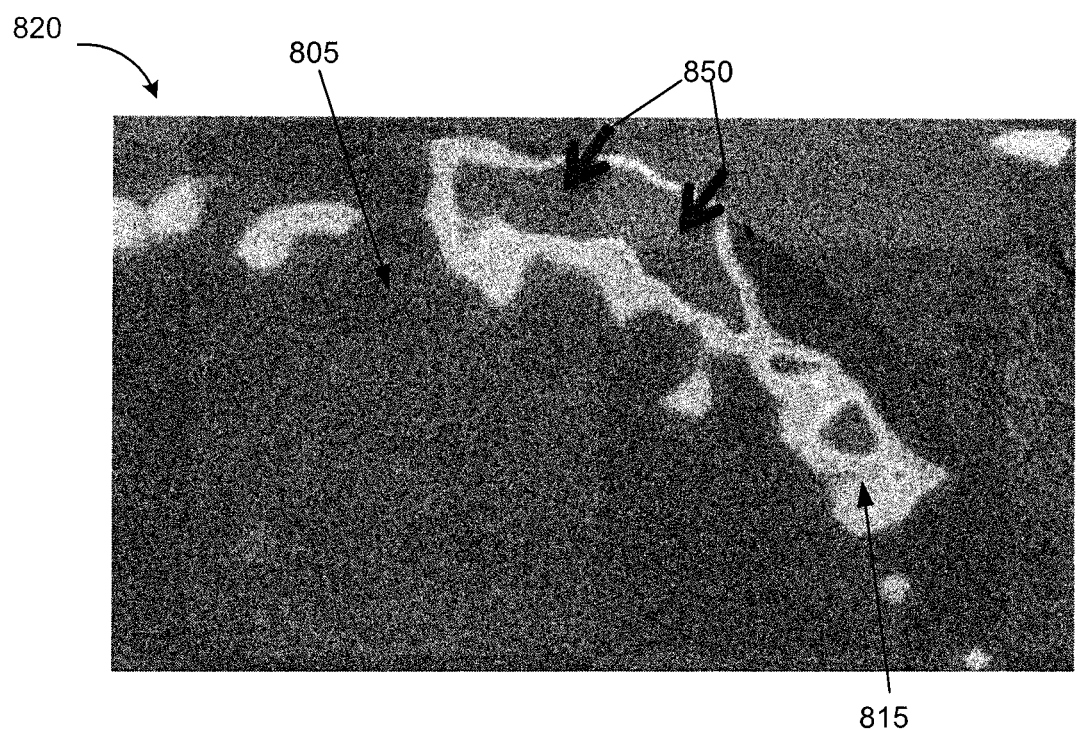
FIG. 8B is a diagram illustrating an overlay of an MS-image on the immunostained image of FIG. 8A showing the localization of an exogenous agent administered to the excised breast cancer tumors.

Referring now to FIG. 8B, shown therein is an overlay image 820 showing the DESI-MS distribution of [Gadoteridol+Na]+ at a m/z of 582.1 overlaid with an image of the breast cancer tumor 805. The sodiated adduct of Gadoteridol 815 localizes to the regions 850 in the periphery of the tumor where the blood vessels of the tumor 805 are located. Analysis of the rest of the image shows similar colocalization with blood vessels throughout the tumor 805. This suggests that the [Gadoteridol+Na]+ of m/z 582.1 adduct colocalizes well with major vasculature within the tumor structure.

Figure 8C:
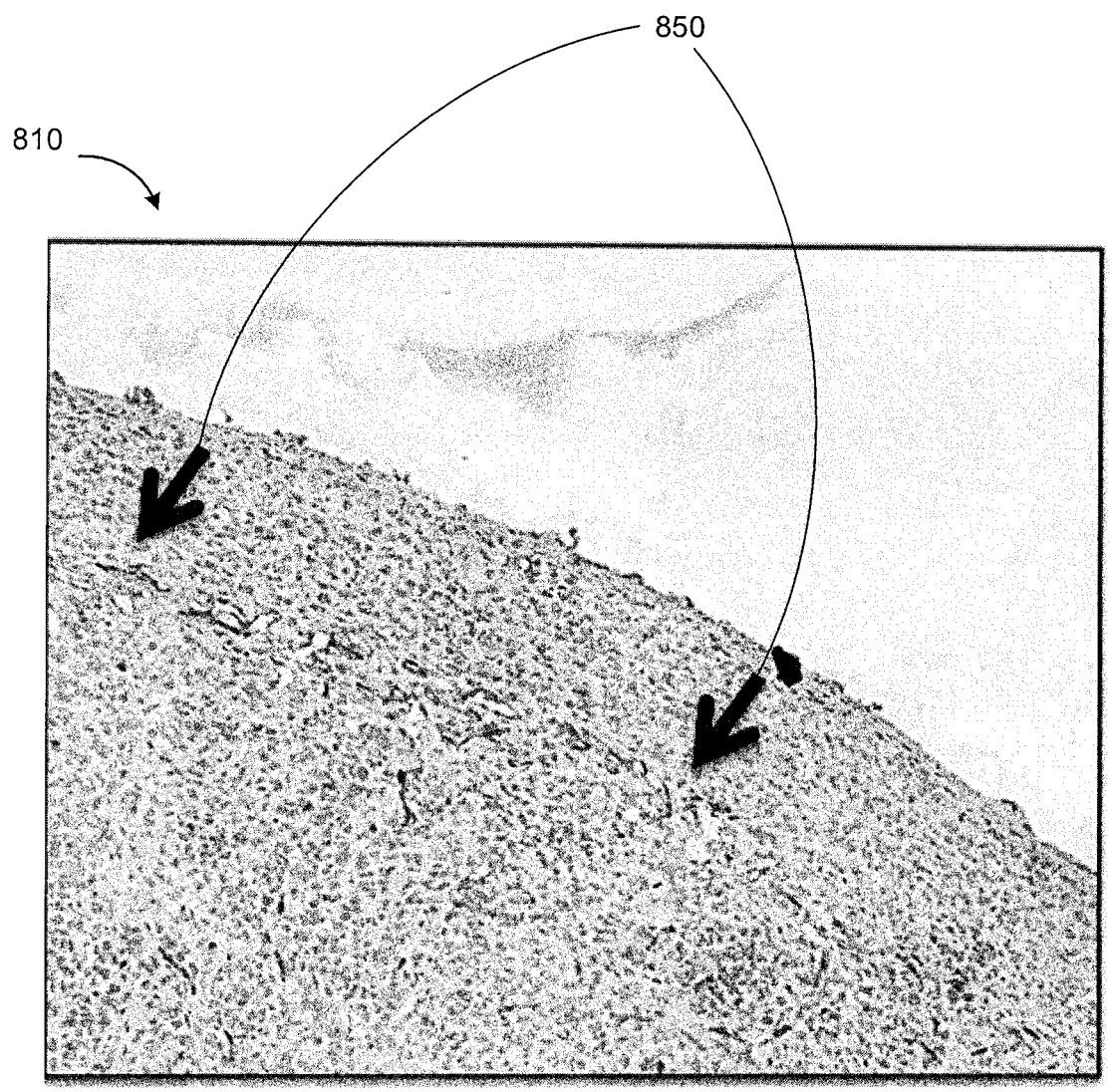
FIG. 8C is a diagram illustrating a zoomed in view of the immunostained image of FIG. 8A.

Referring now to FIG. 8C, shown therein is a zoomed-in image 810 of the boxed area 810 shown in FIG. 8A. The regions 850 of the major tumor vessels can also be seen here.

As discussed above, human breast cancer tumors grown in mice were subjected to ambient two-dimensional DESI-MS imaging to reveal cancer regions from the spatial distribution pattern of the MR contrast agent Gadoteridol. The adduct [Gadoteridol+Na]$^+$, after transvascularization, was seen to localize to the periphery of the tumor where the majority of the tumor vasculature exists, while the [Gadoteridol+K]$^+$ adduct localizes uniformly throughout the tumor core.

Unequivocal identification was achieved through MS/MS analysis of the tissue-borne Gadoteridol, and ion abundances seen in DESI were corroborated with ICP-MS, after extraction. The systems and methods described herein for mapping regions of interest such as tumors using exogenous agent may extend the intraoperative utility of DESI-MS imaging and other high sensitivity imaging modalities to all tumor cases and regions of interest that could be passively targeted with contrast agents. This may allow many tumors for which there are currently no known markers to be mapped.

Prophetic Example #1: Gadoterate

Gadoterate is administered as an exogenous contrast agent by intravenous injection into the tail vein of mice having a tumor under anesthesia with isofluorane. The equipment used to obtain mass spectrometer images and other types of images is the same as that described for the Gadoteridol example. A first MR image is taken at the time of injection and is expected that the tumor site will not yet show the contrast agent in the first MR image. A second MR image is taken at 5 minutes post injection and it is expected to show increased contrast enhancement due to the administration of the exogenous agent. Mass spectrum plots are obtained using DESI-MS on samples from a control breast cancer tumor and a labelled breast cancer tumor. The exogenous agent in the MS images is expected to have the highest signal at the outer edge of the tumor and the exogenous agent appears to penetrate the tumor structure from the periphery.

Prophetic Example #2: Iohexol

Iohexol is administered as an exogenous contrast agent by intravenous injection into the tail vein of mice having a tumor under anesthesia with isofluorane. The equipment used to obtain mass spectrometer images and other types of images is generally the same as that described for the Gadoteridol example except that in this case a CT scanner is used instead of an MRI scanner. Accordingly, a first CT image is taken at the time of injection and is expected that the tumor site will not yet show the contrast agent in the first CT image. A second CT image is taken at a certain time post injection depending on the pharmacokinetics of Iohexol, as is known in the art, and it is expected to show increased contrast enhancement due to the administration of the exogenous agent. Mass spectrum plots are obtained using DESI-MS on samples from a control breast cancer tumor and a labelled breast cancer tumor. The exogenous agent in the MS images is expected to have the highest signal at the outer edge of the tumor and the exogenous agent appears to penetrate the tumor structure from the periphery.

The systems and results described herein illustrate the versatility of intraoperative DESI-MS as a general platform to identify regions of interest such as cancerous regions, or other regions identified earlier in the description, in combination with the administration of a safe, clinically approved, contrast agent. The systems and methods described herein may also provide a platform to glean insights into how passively targeted contrast agents localize within tumor structures.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A method of identifying a region of interest in tissue, the method comprising:
    administering an exogenous agent to the tissue, the exogenous agent being capable of forming a by-product in the tissue;
    analyzing a sample based on the tissue using a high sensitivity platform comprising a mass spectrometer;
    determining a distribution, optionally quantitative, of the by-product of the exogenous agent within the tissue based on the analysis of the sample; and
    identifying the region of interest within the tissue based on the determined distribution of the by-product of the exogenous agent relative to tissue surrounding the region of interest.

2. The method of claim 1, wherein the determining act further comprises determining a distribution of the exogenous agent in addition to the by-product of the exogenous agent.

3. The method of claim 2, further comprising:
    identifying a boundary of the region of interest based on the distribution of at least one of the exogenous agent, and the by-product of the exogenous agent relative to tissue surrounding the region of interest; and
    displaying an image of the tissue with the boundary marked.

4. The method of claim 1, wherein prior to the analyzing act the method comprises
    acquiring the sample from the tissue after administration of the exogenous agent to the tissue; and
    transporting the sample to the mass spectrometer using a transfer line by applying a positive pressure on the transfer line at a first end proximate to the tissue.

5. The method of claim 4, wherein acquiring the sample comprises desorbing the sample from the tissue, the desorbing act selected from applying laser ablation vaporization, desorption electrospray ionization, or radio frequency ablation.

6. The method of claim 4, further comprising ionizing the sample using inductively-coupled plasma, rapid evaporative ionization, or electrospray ionization prior to analyzing the sample unless the administered exogenous agent includes charged particles, or becomes ionized as an adduct.

7. The method of claim 1, wherein prior to the analyzing act the method comprises obtaining the sample from the tissue using an ex vivo sampling technique.

8. The method of claim 1, wherein the method comprises selecting the exogenous agent so that the at least one of the exogenous agent and the by-product of the exogenous agent has at least one of a mass to charge ratio peak and an elemental mass peak that is not endogenous to the tissue.

9. The method of claim 1, further comprising selecting the agent from chelated metal containing agents and tumour specific metalloporphyrins, or chelated metal containing agents being Gadolinium based, ion oxide based, iron-platinum based, manganese based, or chromium based.

10. The method of claim 1, further comprising selecting the exogenous agent from at least one of a metallic element, a heavy atom, and an isotopic variant that is not endogenous to the tissue, a metabolic precursor, an isotopic variant of a metabolic precursor, a moiety of a metabolic precursor or a plurality of exogenous sub-agents.

11. The method of claim 10, wherein the at least one isotopic variant comprises an isotopic variant of an endogenous metabolic precursor, and the method comprises determining the distribution of a by-product of the isotopic variant of the endogenous metabolic precursor.

12. The method of claim 1, wherein the exogenous agent is administered encapsulated in a lipidic structure.

13. The method of claim 1, wherein the sample comprises a tissue sample, an ablated tissue sample, an ablation plume, a liquefied tissue sample, an extraction of the exogenous agent, or an extraction of the by-product of the exogenous agent.

14. A system for identifying a region of interest in tissue, the system comprising:
    a sampling unit configured to acquire a sample based on the tissue after administration of an exogenous agent to the tissue, the exogenous agent being capable of forming a by-product in the tissue; and
    a high sensitivity platform comprising a mass spectrometer, the high sensitivity platform being coupled to the sampling unit to analyze the sample, the high sensitivity platform being configured to determine a distribution, optionally quantitative, of a by-product of the exogenous agent within the tissue based on a spectral analysis of the sample to determine spectral peaks due to the by-product of the exogenous agent that are not endogenous to the tissue and to identify the region of interest based on the determined distribution of the by-product of the exogenous agent relative to tissue surrounding the region of interest.

15. The system of claim 14, wherein the high sensitivity platform is configured to determine a distribution of the exogenous agent in addition to the by-product of the exogenous agent based on a spectral analysis of the sample to determine spectral peaks due to the exogenous agent that are not endogenous to the tissue, and the exogenous agent and the by-product of the exogenous agent having at least one of a mass to charge ratio peak and an elemental mass peak that is not endogenous to the tissue.

16. The system of claim 14, wherein the at least one isotopic variant comprises an isotopic variant of an endogenous metabolic precursor, and the high sensitivity platform is configured to determine the distribution of a by-product of the isotopic variant of the endogenous metabolic precursor.

17. The system of claim 14, wherein the sampling unit comprises at least one of a desorption component configured to desorb the sample from the tissue, a vaporization component configured to vaporize the sample from the tissue, the desorption component comprises a laser ablation device; and an ionization device configured to ionize the sample from the tissue, the ionization device comprising an inductively-coupled plasma ionization device.

18. The system of claim 17, further comprising a transportation unit including a transfer line configured to couple the sampling unit and the mass spectrometer to transport the sample to the mass analyzer unit, wherein the transfer line houses the at least one of the desorption component and the vaporization component.

19. The system of claim 14, further comprising a transportation unit including a transfer line that is configured to couple the sampling unit and the mass spectrometer to transport the sample to the mass analyzer unit and the transfer line is configured to apply a positive pressure on the transfer line at a first end of the transfer line, the first end being proximate the tissue from which the sample is acquired.

20. The system of claim 19, wherein at least one of the sampling unit and the transfer line comprises trackable markings; and the high sensitivity platform is configured to track the trackable markings to identify a location of the tissue where the sample was acquired.

21. The system of claim 14, further comprising a display device; wherein the high sensitivity platform is further configured to identify a boundary of the region of interest; and the display device is configured to display an image of the tissue with the boundary marked.

* * * * *